US009006284B2

(12) United States Patent
Kremmidiotis et al.

(10) Patent No.: US 9,006,284 B2
(45) Date of Patent: Apr. 14, 2015

(54) COMBINATION THERAPY FOR TREATING PROLIFERATIVE DISEASES

(75) Inventors: Gabriel Kremmidiotis, Flagstaff Hill (AU); David Bibby, Henley Beach (AU); Annabell Leske, Allenby Gardens (AU)

(73) Assignee: Bionomics Limited (AU)

(*) Notice: Subject to any disclaimer, the term of this patent is extended or adjusted under 35 U.S.C. 154(b) by 0 days.

(21) Appl. No.: 13/392,473

(22) PCT Filed: Aug. 25, 2010

(86) PCT No.: PCT/AU2010/001097
§ 371 (c)(1),
(2), (4) Date: Feb. 24, 2012

(87) PCT Pub. No.: WO2011/022772
PCT Pub. Date: Mar. 3, 2011

(65) Prior Publication Data
US 2012/0149665 A1 Jun. 14, 2012

(30) Foreign Application Priority Data
Aug. 27, 2009 (AU) ................. 2009904098

(51) Int. Cl.
*A01N 43/08* (2006.01)
*A61K 31/34* (2006.01)
*A61K 45/06* (2006.01)
*A61K 31/09* (2006.01)
*A61K 31/343* (2006.01)
*A61K 31/404* (2006.01)
*A61K 31/407* (2006.01)
*A61K 31/436* (2006.01)

(52) U.S. Cl.
CPC .............. *A61K 45/06* (2013.01); *A61K 31/09* (2013.01); *A61K 31/343* (2013.01); *A61K 31/404* (2013.01); *A61K 31/407* (2013.01); *A61K 31/436* (2013.01)

(58) Field of Classification Search
None
See application file for complete search history.

(56) References Cited

U.S. PATENT DOCUMENTS

| 5,340,062 | A | 8/1994 | Heggestad |
| 5,886,025 | A | 3/1999 | Pinney |
| 6,162,930 | A | 12/2000 | Pinney et al. |
| 6,251,090 | B1 | 6/2001 | Avery et al. |
| 6,299,603 | B1 | 10/2001 | Hecker et al. |
| 6,350,777 | B2 | 2/2002 | Pinney et al. |
| 6,849,656 | B1 | 2/2005 | Pinney et al. |
| 7,071,190 | B2 | 7/2006 | Goff et al. |
| 7,429,681 | B2 | 9/2008 | Pinney et al. |
| 7,456,214 | B2 | 11/2008 | Pinney et al. |
| 2005/0064010 | A1 | 3/2005 | Cooper et al. |
| 2005/0074497 | A1 | 4/2005 | Schultz |
| 2005/0208103 | A1 | 9/2005 | Adamis et al. |
| 2005/0250737 | A1 | 11/2005 | Hughes et al. |
| 2012/0149665 | A1 | 6/2012 | Kremmidiotis et al. |
| 2012/0157521 | A1 | 6/2012 | Kremmidiotis |

FOREIGN PATENT DOCUMENTS

| CN | 1527704 A | 9/2004 |
| WO | WO-98/39323 | 9/1998 |
| WO | WO-0119794 A2 | 3/2001 |
| WO | WO-0168654 A2 | 9/2001 |
| WO | WO-02060872 A1 | 8/2002 |
| WO | WO-03006002 A1 | 1/2003 |
| WO | WO-2005/113532 A1 | 12/2005 |
| WO | WO-2006/084338 A1 | 8/2006 |
| WO | WO-2007/087684 A1 | 8/2007 |
| WO | WO 2008027013 A2 * | 3/2008 |
| WO | WO-2008/070908 A1 | 6/2008 |
| WO | WO-2011/022772 A1 | 3/2011 |
| WO | WO-2011/022781 A1 | 3/2011 |

OTHER PUBLICATIONS

Neidle, Cancer Drug Design and Discovery, Elsevier/Academic Press, 2008, pp. 427-431.*
Fan et al., Bioorganic & Medicinal Chemistry Letters, vol. 7, No. 24, pp. 3107-3112.*
Rischin et al. "Clinical, Pharmacodynamic, and Pharmacokinetic Evaluation of BNC105P: A Phase I Trial of a Novel Vascular Disrupting Agent and Inhibitor of Cancer Cell Proliferation", Clin.Cancer.Res., 2011, vol. 17, No. 15, pp. 5152-5160.*
Kremmidiotis et al. Mol.CancerTher., 2010, vol. 9, pp. 1562-1573.*
Campostrini et al., "Proteomic Analysis of Anti-Angiogenic Effects by a Combined Treatment with Vinblastine and Rapamycin in an Endothelial Cell Line," Proteomics, 2006, 6, pp. 4420-4431.
Chou, "Theoretical Basis, Experimental Design, and Computerized Simulation of Synergism an Antagonism in Drug Combination Studies," Pharmacological Reviews, 2006, vol. 58, No. 3, pp. 621-681.
Gill et al., "An Efficient Synthesis and Substitution of 3-Aroyl-2-bromobenzo[b]furans," J. Org. Chem., 2008, vol. 73, No. 3, pp. 1131-1134.
International Search Report of the International Searching Authority, the Australian Patent Office, for International Application No. PCT/AU2010/001097, dated Oct. 7, 2010, 5 pages.
Liou et al., "Concise Synthesis and Structure-Activity Relationships of Combrestastatin A-4 Analogues, 1-Acroylindoles and 3-Aroylindoles, as Novel Classes of Potent Antitubulin Agents," Journal of Medicinal Chemistry, Aug. 2004, 47(17), pp. 4247-4257.
Ma et al., "Anti-Microtubule Activity of Tubeimoside I and its Colchicine Binding Site of Tubulin," Cancer Chemother Pharmacol, 2008, 62, pp. 559-568.

(Continued)

*Primary Examiner* — Jeffrey S Lundgren
*Assistant Examiner* — Stephanie Springer
(74) *Attorney, Agent, or Firm* — Wilmer Cutler Pickering Hale and Dorr LLP

(57) ABSTRACT

A pharmaceutical composition of a tubulin polymerisation inhibitor and an mTOR inhibitor and a method of treating proliferative disease with a combination of a tubulin polymerisation inhibitor and an mTOR inhibitor.

11 Claims, 7 Drawing Sheets

(56) References Cited

OTHER PUBLICATIONS

Marimpietri et al., "Combined Therapeutic Effects of Vinblastine and Rapamycin on Human Neuroblastoma Growth, Apoptosis, and Angiogenesis," Clinical Cancer Research, Jul. 2007, 13, pp. 3977-3988.

Marimpietri et al., "Synergistic Inhibition of Human Neuroblastoma-Related Angiogenesis by Vinblastine and Rapamycin," Oncogene, 2005, 24, pp. 6785-6795.

Pettit et al., "Antineoplastic Agents 322. Synthesis of Combretastatin A-4 Prodrugs," Anti-Cancer Drug Design, 1995, 10, pp. 299-309.

Ribatti et al., "In vivo Inhibition of Human Hepatocellular Carcinoma Related Angiogenesis by Vinblastine and Rapamycin," Histol Histopathol, 2007, 22, pp. 285-289.

Tozer et al., "Disrupting Tumour Blood Vessels," Nature Reviews/Cancer, vol. 5, Jun. 2005, pp. 423-435.

Wu et al., "Synthesis and Evaluation of 3-Aroylindoles as Anticancer Agents: Metabolite Approach," Journal of Medicinal Chemistry, 2009, vol. 52, No. 15, pp. 4941-4945.

Arsham, et al., "A Novel Hypoxia-Inducible Factor-independent Hypoxic Response Regulating Mammalian Target of Rapamycin and Its Targets," The Journal of Biological Chemistry, vol. 278, No. 32, pp. 29655-29660 (2003).

Ei-Emir, et al., "Tumour Parameters Affected by Combretastatin A-4 Phosphate Therapy in a Human Colorectal Xenograft Model in Nude Mice," European Journal of Cancer, vol. 41, pp. 799-806 (2005).

Negrier, et al., "Temsirolimus and Bevacizumab, or Sunitonib, or Interferon Alfa and Bevacizumab for Patients with Advanced Renal Cell Carcinoma (TORAVA): a randomised Phase 2 Trial," Lancet Oncology, Published at www.thelancet.com/oncology, vol. 12, pp. 673-680 (Jul. 10, 2011).

Sarantopoulos, et al., "A Phase I/II Trial of BNC105P with Everolimus in Metastatic Renal Cell Carcinoma (mRCC) Patients: Updated Phase I Results of the DisrupTOR-1 Trial (Hoosier Oncology Group)," ASCO 2013, Abstract ID 4563, Protocol #GU09-145 (1 pg.).

Ibrahim, M.A. et al., "Vascular disrupting agent for neovascular age related macular degeneration: a pilot study of the safety and efficacy of intravenous combretastatin a-4 phosphate," BMC Pharmacology & Toxicology, vol. 14, No. 7, 10 pages (2013).

Monk, K.A. et al., "Design, synthesis, and biological evaluation of combretastatin nitrogen-containing derivatives as inhibitors of tubulin assembly and vascular disrupting agents," Bioorganic & Medicinal Chemistry, vol. 14, pp. 3231-3244 (2006).

* cited by examiner

| CELL LINE | Indication | Temsirolimus | |
|---|---|---|---|
| | | $ED_{50}$ | $ED_{75}$ |
| Caki-1 | Kidney, Clear Cell Carcinoma | 0.719 | 1.059 |
| A498 | Kidney, carcinoma | 0.845 | 0.442 |
| Calu-6 | Lung, anaplastic carcinoma | 0.782 | 0.765 |
| A4549 | Lung carcinoma | 0.785 | 0.887 |
| SK-OV-3 | Ovary adenocarcinoma | 0.965 | 0.986 |

CI=0.1-0.9 Synergistic
CI=0.9-1.1 Additive
CI=>1.1 No additive benefit

FIGURE 2

COMBINATION THERAPY FOR TREATING PROLIFERATIVE DISEASES

FIELD OF THE INVENTION

The present invention relates generally to new chemical combinations and methods for their use in the treatment of proliferative diseases and in particular cancer.

BACKGROUND OF THE INVENTION

Cancer is typically treated with either chemotherapy and/or radiation therapy. While often effective to destroy a significant amount of tumour cells, such therapies often leave behind a number of tumour cells that are resistant to the treatment. These resistant cells can proliferate to form new tumors that are then resistant to treatment. The use of known combinations of chemotherapeutic drugs has given rise to multidrug resistant ('MDR') tumour cells.

The mode of proliferative diseases, such as cancer, is multifactorial. For instance, research over the last forty years has led to the realisation that cytotoxic agents (or anti-proliferative agents) includes anti-metabolic agents which interfere with microtubule formulation, alkylating agents which are able to cross-link DNA, platinum based agents which are able to interfere with DNA alkylation by blocking DNA replication, antitumor antibiotic agents, topoisomerase inhibitors, etc. In the treatment of such diseases drugs with different mechanisms may be combined (i.e, combination therapies) with beneficial effects including the effective treatment of MDR tumour cells and the minimisation of side effects such as undesirable cytotoxicity. The difficulty here is though that not all known antiproliferative agents provide useful or beneficial effects in combination and accordingly research in many laboratories is presently focused on developing new and useful anti-proliferative combination partners.

SUMMARY OF THE INVENTION

The present invention provides a pharmaceutical combination for treating a proliferative disease comprising: (a) a tubulin polymerisation inhibitor, and (b) a mTOR inhibitor.

The present invention also provides a method for treating a proliferative disease including the step of administering to a patient in need thereof: (a) a tubulin polymerisation inhibitor, and (b) a mTOR inhibitor.

The present invention also provides the use of: (a) a tubulin polymerisation inhibitor, and (b) a mTOR inhibitor, in the manufacture of a medicament for the treatment of a proliferative disease.

The present invention also provides the use of: (a) a tubulin polymerisation inhibitor in the manufacture of a medicament for the treatment of a proliferative disease to be used in combination with (b) a mTOR inhibitor.

The present invention also provides the use of: (b) a mTOR inhibitor in the manufacture of a medicament for the treatment of a proliferative disease to be used in combination with (a) a tubulin polymerisation inhibitor.

The present invention further provides a pharmaceutical composition comprising (a) a tubulin polymerisation inhibitor, and (b) a mTOR inhibitor.

Surprisingly it has been found that the effects in treating proliferative diseases with a combination which comprises: (a) a tubulin polymerisation inhibitor, and (b) a mTOR inhibitor, are greater than the effects that can be achieved with either (a) or (b) alone. That is, the present combinations have been found to possess an additive or synergistic effect.

BRIEF DESCRIPTION OF THE FIGURES

FIG. 2 Table showing combination index values for combination of Example 2 compound with temsirolimus with respect to various cancer cell lines.

DESCRIPTION OF THE PREFERRED EMBODIMENTS

Figure 1:
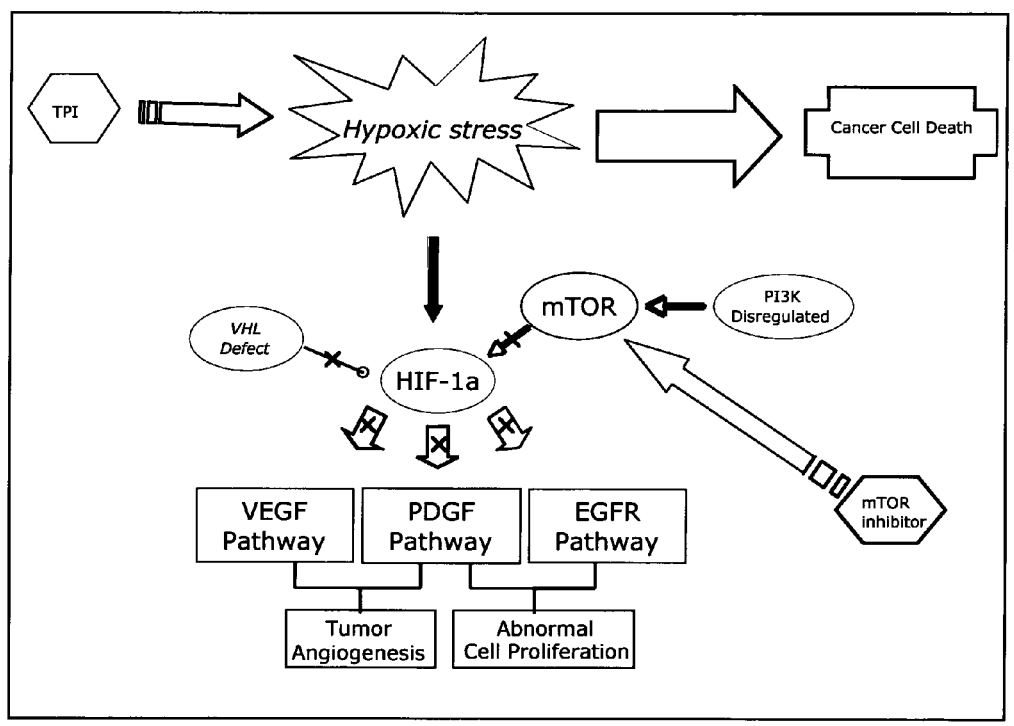
FIG. 1 Schematic diagram illustrating the proposed effects of the combination of the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Combination Partner (a); Tubulin Polymerisation Inhibitor (TPI)

As used herein the term "tubulin polymerisation inhibitor" refers to any and all compounds which directly interact with tubulin and inhibit tubulin polymerisation and as a consequence interferes with the physiological function of microtubules. Tubulin polymerisation inhibitors (TPI's) are often referred to as microtubule "destabilising" agents. Such compounds should be contrasted with tubulin interacting compounds like taxanes and epothilones which stabilise tubulin polymers and inhibit tubulin depolymerisation (i.e., microtubule stabilising agents)).

Examples of suitable TPI's include:
(i) Synthetic Compounds
   ABT-751 (E7010, Abbott)
   MPC-6827 (Azixa™, Myriad Pharmaceuticals)
   AEZS-112 (ZEN-012, Eterna Zentaris)
   CYT997 (Cytopia)
   MN-029 (Denibulin, MediciNova/Angiogene)
   EPC2407 (EpiCept)
   ZIO-301 (Indibulin, Ziopharm Oncology)

(ii) Natural Products Derivatives
  Vinflunine (Javlor, Pierre Fabre Medicament) as well as other vinca alkaloids (e.g., vinblastin, vincristine, and vinorelbine)
  Combretastatins
    CA4 (Zybrestat™, OXiGENE)
    Oxi4503 (OXiGENE)
    AVE8062 (AC7700, Sanofi Aventis)
  Eribulin Mesylate (E7389, Eisai)
  Dolastatin 10 (NCI)
  Tasidotin (synthadotin, Genzyme)
  2-methoxyestradiol (2ME2 or Panzem®, EntreMed)
  E7974 (Eisai)
  NPI-2358 (Nereus Pharmaceuticals)

Microtubules are filamentous polymers that are key components of the cell cytoskeleton. They are dynamic structures fluctuating between states of polymerisation and depolymerisation. This property enables microtubules to modulate cell shape, adhesion, migration and proliferation. TPI's directly disrupt microtubule polymerisation processes and consequently have the ability to effect cell shape changes and inhibit cell proliferation. These properties are central to the use of TPI's as therapeutics for the treatment of cancer and in the combinations of the present invention.

TPI compounds are important in the treatment of cancers primarily as a result of their capacity to selectively shut down blood flow through a tumour. Targeting tubulin polymerisation inhibition has been a very well validated anti-cancer approach through the development and now extensive clinical use of chemotherapeutic TPI's agents.

TPI's can be classified based on their specific tubulin binding site.

Binding of vinca alkaloids to tubulin defines a site that mediates the tubulin destabilization activity seen with these compounds. The 'vinca' site has been shown to directly bind a number of compounds that effect destabilization of tubulin.

Colchicine binding to tubulin defines an independent binding site that like in the case of the 'vinca' site causes destabilization of tubulin. Although TPI's binding to the 'vinca' sites have been successful as anti-cancer chemotherapeutics, 'colchicine' site binders have been in comparison neglected, possibly due to the lack of therapeutic margins offered by colchicine. However, more recently a number of 'colchicine' site binding agents have been described that have the ability to cause disruption of blood vessels within solid tumors. These TPI's are referred to as Vascular Disruption Agents (VDA). Many of the 'colchicine' site binding agents that exhibit VDA capability are based on natural products such as combretastatins (CA4P, OXi-4503, AVE-8062), colchicines (ZD6126) and phenylahistin (NPI-2358) while others are synthetic compounds (MN-029 and EPC2407).

TPIs act as VDAs because they interfere with microtubule integrity, leading to cytoskeletal changes of the endothelial cells that line the blood vessels of the tumour. As a result, these usually flat cells become more rounded, and lose their cell to cell contact. These events lead to narrowing of tumour blood vessels and ultimately occlusion of blood flow through the vessels. The tumour selectivity associated with these agents results from the fact that tumour vasculature is weaker and more prone to collapse than normal vasculature. Nonetheless, a number of the dose limiting toxicities associated with VDAs are due to a reduction in blood flow in healthy tissues.

In a preferred embodiment the TPI is a TPI which acts by binding to the colchicine site of tubulin. Assays which can be used to determine if a TPI acts at the colchicine biding site of tubulin are known in the art, such as in Ma, R et al, Cancer Chemother. Pharmacol., 2008, September 62(4) 559-68.

In another embodiment the TPI is a TPI which acts at the colchicine binding site and is based on annulated furans (e.g., benzofurans, furo[2,3-d]pyrimidin-2(1H)-ones, etc), benzothiophene and indole structural scaffolds, such as those disclosed in U.S. Pat. Nos. 7,456,214, 7,429,681, 7,071,190, 6,849,656, 5,886,025, 6,162,930, 6,350,777, 5,340,062, WO 06/084338, WO 02/060872, WO 07/087,684, and WO 08/070,908.

In an embodiment the TPI is selected from a TPI disclosed in WO 06/084338, WO 07/087,684, or WO 08/070,908.

In an embodiment the TPI is selected from a compound of formula (I) and salts thereof (I)

wherein;
  X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;
  $R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

L represents C=O, O, S, SO, $SO_2$, Se, SeO, $SeO_2$, C=NZ', or NR' where Z' is H, optionally substituted alkyl, optionally substituted aryl or optionally substituted amino; and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

$R^{2A}$-$R^{2E}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{2A}$ and $R^{2B}$, $R^{2B}$ and $R^{2C}$, $R^{2C}$ and $R^{2D}$, and $R^{2D}$ and $R^{2E}$, together form an optionally substituted aryl, optionally substituted heterocyclyl, optionally substituted heteroaryl, optionally substituted cycloalkyl, or optionally substituted cycloalkenyl; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted heterocyclyl, optionally substituted acyl and optionally substituted oxyacyl, or NR'"NR'", where each R'" independently represents H, optionally substituted alkyl, optionally substituted alkenyl, optionally substituted alkynyl, optionally substituted aryl and optionally substituted heteroaryl.

In some embodiments $R^{1A}$-$R^{1B}$ and $R^{2A}$-$R^{2E}$ are independently selected from the following groups:

alkyl group, preferably methyl and ethyl;

substituted alkyl group, preferably 1-hydroxyethyl, 1-thioethyl, methoxyiminomethyl, ethoxyiminomethyl, 1-(hydroxyimino)ethyl, 1-(hydroxyimino)propyl, 1-hydrazinoethyl, 1-hydrazinopropyl, hydroxyiminomethyl, 2-oxopropyl, 2-oxobutyl, 3-oxobutyl, 3-oxopentyl, nitromethyl, 1-nitromethyl, and 2-nitroethyl;

acyl group, preferably formyl acetyl, propionyl, benzoyl (optionally substituted with methyl, methoxy, halogen, nitro, trifluoromethyl or cyano);

alkoxy group, preferably methoxy and ethoxy;

oxyacyl group, preferably methoxycarbonyl, ethoxycarbonyl, propoxycarbonyl, butyloxycarbonyl, isobutyloxycarbonyl;

acyloxy group, preferably acetoxy and propioxy;

substituted arylalkyl group, preferably 1-hydroxybenzyl, and 1-thiobenzyl;

sulfinyl group, preferably methylsulfinyl, ethylsulfinyl, benzene sulfinyl (optionally substituted with methyl, methoxy, halogen, nitro, trifluoromethane or cyano), methoxysulfinyl, ethoxysulfinyl;

sulfonyl group, preferably methylsulfonyl, ethylsulfonyl, benzenesulfonyl (optionally substituted with methyl, methoxy, halogen, nitro, trifluoromethane or cyano), methoxycarbo, trifluoromethane;

oxyacylamino group, preferably methoxycarbonylamido, and ethoxycarbonyl amido;

oxythioacyl group, preferably methoxythiocarbonyl and ethoxythiocarbonyl;

thioacyloxy group, preferably thionoacetoxy and thionopropionoxy;

sulphinylamino group, preferably methylsulfinylamino, ethylsulfinylamino, and benzenesulfinylamino (optionally substituted with methyl, methoxy, halogen, nitro, trifluoromethane or cyano);

amino group;

substituted amino groups, preferably residues of L-valine, D-valine, L-alanine, D-alanine, aspartic acid, and alanylserine, N-methylamino, and N,N'-dimethylamino;

sulphonylamino group, preferably methylsulfonylamino, ethylsulfonylamino and benzene sulfonylamino (optionally substituted with methyl, methoxy, halogen, nitro, trifluoromethane or cyano);

oxysulfinylamino group, preferably methoxysulfinylamino and ethoxysulfinylamino;

oxysulfonylamino group, preferably methoxysulfonylamino and ethoxysulfonylamino;

optionally substituted alkenyl group, preferably, 1-propenyl, vinyl, nitrovinyl, cyano vinyl, or trifluorovinyl and styryl (optionally substituted with methyl, methoxy, halogen, nitro, trifluoromethane or cyano);

alkynyl group, preferably 1-propynyl, ethynyl or trimethylsilylethynyl.

In one embodiment $R^{2D}$, $R^{2C}$, and $R^{2B}$ are methoxy and L is a carbonyl group (C=O).

Accordingly, in this embodiment the TPIs of the present invention are represented by formula (Ia)

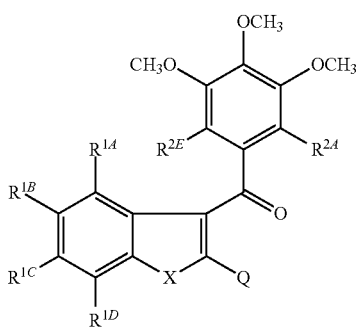

(Ia)

wherein;
- X represents O, S, SO, SO$_2$, Se, SeO, SeO$_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;
- $R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;
- $R^{1C}$ represents $C_{1-3}$ alkoxy, $C_{1-3}$ alkylthio, $C_{1-3}$ alkylamino, or $C_{1-3}$ dialkylamino;
- $R^{1D}$ represents hydroxy or amino;
- $R^{2A}$ and $R^{2E}$ independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihaloethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; and
- Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R' independently represents, H, optionally substituted alkyl, optionally substituted alkenyl, optionally substituted alkynyl, optionally substituted aryl, optionally substituted heteroaryl, optionally substituted heterocyclyl, optionally substituted acyl and optionally substituted oxyacyl, or NR'''NR''', where each R''' independently represents H, optionally substituted alkyl, optionally substituted alkenyl, optionally substituted alkynyl, optionally substituted aryl and optionally substituted heteroaryl.

In another embodiment, $R^{1A}$, $R^{1B}$, $R^{2A}$ and $R^{2E}$ represent H and $R^{1C}$ represents $C_{1-3}$ alkoxy.

Accordingly, in this embodiment the TPI of the present invention is represented by formula (Ib)

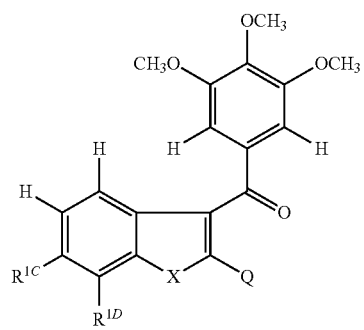

(Ib)

wherein;
- X represents O, S, SO, SO$_2$, Se, SeO, SeO$_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1C}$ represents $C_{1-3}$ alkoxy;

$R^{1D}$ represents hydroxy or amino;

Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted acyl and optionally substituted oxyacyl, or NR'''NR''', where each R''' independently represents H, optionally substituted alkyl, optionally substituted alkenyl, optionally substituted alkynyl, optionally substituted aryl and optionally substituted heteroaryl.

In a preferred embodiment $R^{1C}$ represents methoxy.

For the compounds represented by formulae I, Ia and Ib, X is preferably selected from O, S and NR. More preferably X is O or NR and most preferably X is O.

Accordingly, in another embodiment the TPI is represented by formula II:

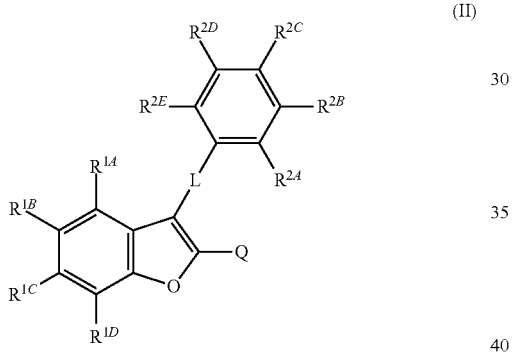

(II)

wherein;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

L represents C=O, O, S, SO, $SO_2$, Se, SeO, $SeO_2$, C=NZ% or NR' where Z' is H, optionally substituted alkyl, optionally substituted aryl or optionally substituted amino; and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

$R^{2A}$-$R^{2E}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{2A}$ and $R^{2B}$, $R^{2B}$ and $R^{2C}$, $R^{2C}$ and $R^{2D}$, and $R^{2D}$ and $R^{2E}$, together form an optionally substituted aryl, optionally substituted heterocyclyl, optionally substituted heteroaryl, optionally substituted cycloalkyl, or optionally substituted cycloalkenyl; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted heterocyclyl, optionally substituted aryl, optionally substituted heteroaryl, optionally substituted acyl and optionally substituted oxyacyl, or NR'''NR''', where each R''' independently represents H, optionally substituted alkyl, optionally substituted alkenyl, optionally substituted alkynyl, optionally substituted aryl and optionally substituted heteroaryl.

In this embodiment it is preferred that L is a carbonyl group (C=O). Also, preferably at least one of $R^{2D}$, $R^{2C}$ or $R^{2B}$ represents a hydroxy or $C_{1-3}$ alkoxy group. More preferably when X=O, L is a carbonyl group an $R^{2D}$, $R^{2C}$ and $R^{2B}$ represent methoxy. Even more preferably when X=O, L is a carbonyl group, $R^{2D}$, $R^{2C}$, and $R^{2B}$ represent methoxy and $R^{1A}$, $R^{1B}$, $R^{2A}$, $R^{2E}$ are H.

Furthermore, for the compounds of formula (I), (Ia), (Ib) and (II) it is preferred that Q represents H, CN, optionally substituted $C_{2-4}$ alkynyl, optionally substituted $C_{2-6}$ alkenyl, optionally substituted $C_{1-4}$ alkyl, hydroxy, optionally substituted oxyacyl, NR"R", SR" (where each R" is independently H, optionally substituted $C_{1-4}$alkyl, optionally substituted heterocyclyl, optionally substituted heteroaryl), NR'''NR''' (where each R''' is independently H, $C_{1-3}$ alkyl), optionally substituted acylamino, or halogen.

In some embodiments Q is independently selected from the following groups:

H;
CN;
halogen, preferably Br or Cl;
alkyl group, preferably methyl, ethyl, propyl, butyl;
substituted alkyl group, preferably amino, oxyacylaminoalkyl and oxysulphonylaminoalkyl;
optionally substituted alkenyl, preferably ethenyl, 2-alkylethenyl, 2-oxyacylethenyl, 2-aminoacylethenyl;
optionally substituted alkynyl, preferably ethynyl, 2-alkylethynyl;
optionally substituted oxyacyl;
OR", preferably hydroxy, methoxy, ethoxy;
NR"R", preferably $NH_2$, alkylamino, dialkylamino, heteroarylamino, aminoalkylamino, hydroxyalkylamino, alkoxyalkylamino, oxyacylalkylamino, oxyacylaminoalkylamino, guanidinoalkylamino;
SR", preferably alkylthio, aminoalkylthio, heteroarylthio, aminoalkylthio, hydroxyalkylthio, alkoxyalkylthio, oxyacylalkylthio, oxyacylaminoalkylthio, guanidinoalkylthio;
hydrazine.

Chemical Definitions

"Alkyl" refers to monovalent alkyl groups which may be straight chained or branched and preferably have from 1 to 10 carbon atoms or more preferably 1 to 6 carbon atoms, and even more preferably 1 to 3 carbon atoms. Examples of such alkyl groups include methyl, ethyl, n-propyl, iso-propyl, n-butyl, iso-butyl, n-hexyl, and the like.

"Alkylene" refers to divalent alkyl groups preferably having from 1 to 10 carbon atoms and more preferably 1 to 6 carbon atoms, and even more preferably 1 to 3 carbon atoms. Examples of such alkylene groups include methylene (—$CH_2$—), ethylene (—$CH_2CH_2$—), and the propylene isomers (e.g., —$CH_2CH_2CH_2$— and —$CH(CH_3)CH_2$—), and the like.

"Aryl" refers to an unsaturated aromatic carbocyclic group having a single ring (eg., phenyl) or multiple condensed rings (eg., naphthyl or anthryl), preferably having from 6 to 14 carbon atoms. Examples of aryl groups include phenyl, naphthyl and the like.

"Arylene" refers to a divalent aryl group wherein the aryl group is as described above.

"Aryloxy" refers to the group aryl-O— wherein the aryl group is as described above.

"Arylalkyl" refers to -alkylene-aryl groups preferably having from 1 to 10 carbon atoms in the alkylene moiety and from 6 to 10 carbon atoms in the aryl moiety. Such arylalkyl groups are exemplified by benzyl, phenethyl and the like.

"Arylalkoxy" refers to the group arylalkyl-O— wherein the arylalkyl group are as described above. Such arylalkoxy groups are exemplified by benzyloxy and the like.

"Alkoxy" refers to the group alkyl-O— where the alkyl group is as described above. Examples include, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkenyl" refers to a monovalent alkenyl group which may be straight chained or branched and preferably have from 2 to 10 carbon atoms and more preferably 2 to 6 carbon atoms and have at least 1 and preferably from 1-2, carbon to carbon, double bonds. Examples include ethenyl (—CH=$CH_2$), n-propenyl (—$CH_2$CH=$CH_2$), iso-propenyl (—$C(CH_3)$=$CH_2$), but-2-enyl (—$CH_2$CH=$CHCH_3$), and the like.

"Alkenyloxy" refers to the group alkenyl-O— wherein the alkenyl group is as described above.

"Alkenylene" refers to divalent alkenyl groups preferably having from 2 to 8 carbon atoms and more preferably 2 to 6 carbon atoms. Examples include ethenylene (—CH=CH—), and the propenylene isomers (e.g., —$CH_2$CH=CH— and —$C(CH_3)$=CH—), and the like.

"Alkynyl" refers to alkynyl groups preferably having from 2 to 10 carbon atoms and more preferably 2 to 6 carbon atoms and having at least 1, and preferably from 1-2, carbon to carbon, triple bonds. Examples of alkynyl groups include ethynyl (—C≡CH), propargyl (—$CH_2$C≡CH), pent-2-ynyl (—$CH_2$C≡$CCH_2$—$CH_3$), and the like.

"Alkynyloxy" refers to the group alkynyl-O— wherein the alkynyl groups is as described above.

"Alkynylene" refers to the divalent alkynyl groups preferably having from 2 to 8 carbon atoms and more preferably 2 to 6 carbon atoms. Examples include ethynylene (—C≡C—), propynylene (—$CH_2$—C≡C—), and the like.

"Acyl" refers to groups H—C(O)—, alkyl-C(O)—, cycloalkyl-C(O)—, aryl-C(O)—, heteroaryl-C(O)— and heterocyclyl-C(O)—, where alkyl, cycloalkyl, aryl, heteroaryl and heterocyclyl are as described herein.

"Oxyacyl" refers to groups HOC(O)—, alkyl-OC(O)—, cycloalkyl-OC(O)—, aryl-OC(O)—, heteroaryl-OC(O)—, and heterocyclyl-OC(O)—, where alkyl, cycloalkyl, aryl, heteroaryl and heterocyclyl are as described herein.

"Amino" refers to the group —NR*R* where each R* is independently hydrogen, alkyl, cycloalkyl, aryl, heteroaryl, and heterocyclyl and where each of alkyl, cycloalkyl, aryl, heteroaryl and heterocyclyl is as described herein.

"Aminoacyl" refers to the group —C(O)NR*R* where each R* is independently hydrogen, alkyl, cycloalkyl, aryl, heteroaryl, and heterocyclyl and where each of alkyl, cycloalkyl, aryl, heteroaryl and heterocyclyl is as described herein.

"Aminoacylamino" refers to the group —NR*C(O) NR*R* where each R* is independently hydrogen, alkyl, cycloalkyl, aryl, heteroaryl, and heterocyclyl and where each of alkyl, cycloalkyl, aryl, heteroaryl and heterocyclyl is as described herein.

"Acylamino" refers to the group —NR*C(O)R* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Acyloxy" refers to the groups —OC(O)-alkyl, —OC(O)-aryl, —C(O)O-heteroaryl, and —C(O)O-heterocyclyl where alkyl, aryl, heteroaryl and heterocyclyl are as described herein.

"Aminoacyloxy" refers to the groups —OC(O)NR*-alkyl, —OC(O)NR*-aryl, —OC(O)NR*-heteroaryl, and —OC(O)NR*-heterocyclyl where R* is independently hydrogen, alkyl, cycloalkyl, aryl, heteroaryl, and heterocyclyl and where each of alkyl, cycloalkyl, aryl, heteroaryl and heterocyclyl is as described herein.

"Oxyacylamino" refers to the groups —NR*C(O)O-alkyl, —NR*C(O)O-aryl, —NR*C(O)O-heteroaryl, and NR*C(O)O-heterocyclyl where R* is independently hydrogen, alkyl, cycloalkyl, aryl, heteroaryl, and heterocyclyl and where each of alkyl, cycloalkyl, aryl, heteroaryl and heterocyclyl is as described herein.

"Oxyacyloxy" refers to the groups —OC(O)O-alkyl, —O—C(O)O-aryl, —OC(O)O-heteroaryl, and —OC(O)O-heterocyclyl where alkyl, cycloalkyl, aryl, heteroaryl, and heterocyclyl are as described herein.

"Acylimino" refers to the groups —C(NR*)—R* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Acyliminoxy" refers to the groups —O—C(NR*)—R* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Oxyacylimino" refers to the groups —C(NR*)—OR* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Cycloalkyl" refers to cyclic alkyl groups having a single cyclic ring or multiple condensed rings, preferably incorporating 3 to 8 carbon atoms. Such cycloalkyl groups include, by way of example, single ring structures such as cyclopropyl, cyclobutyl, cyclopentyl, cyclohexyl, cyclooctyl, and the like, or multiple ring structures such as adamantanyl, and the like.

"Cycloalkenyl" refers to cyclic alkenyl groups having a single cyclic ring and at least one point of internal unsaturation, preferably incorporating 4 to 8 carbon atoms. Examples of suitable cycloalkenyl groups include, for instance, cyclobut-2-enyl, cyclopent-3-enyl, cyclohex-4-enyl, cyclooct-3-enyl and the like.

"Halo" or "halogen" refers to fluoro, chloro, bromo and iodo.

"Heteroaryl" refers to a monovalent aromatic heterocyclic group which fulfils the Hückel criteria for aromaticity (ie. contains $4n+2\pi$ electrons) and preferably has from 2 to 10 carbon atoms and 1 to 4 heteroatoms selected from oxygen, nitrogen, selenium, and sulfur within the ring (and includes oxides of sulfur, selenium and nitrogen). Such heteroaryl groups can have a single ring (eg., pyridyl, pyrrolyl or N-oxides thereof or furyl) or multiple condensed rings (eg., indolizinyl, benzoimidazolyl, coumarinyl, quinolinyl, isoquinolinyl or benzothienyl).

"Heterocyclyl" refers to a monovalent saturated or unsaturated group having a single ring or multiple condensed rings, preferably from 1 to 8 carbon atoms and from 1 to 4 heteroatoms selected from nitrogen, sulfur, oxygen, selenium or phosphorous within the ring. The most preferred heteroatom is nitrogen.

Examples of heterocyclyl and heteroaryl groups include, but are not limited to, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isothiazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazoles, oxadiazole, oxatriazole, tetrazole, thiazolidine, thiophene, benzo[b]thiophene, morpholino, piperidinyl, pyrrolidine, tetrahydrofuranyl, triazole, and the like.

"Heteroarylene" refers to a divalent heteroaryl group wherein the heteroaryl group is as described above.

"Heterocyclylene" refers to a divalent heterocyclyl group wherein the heterocyclyl group is as described above.

"Thio" refers to groups H—S—, alkyl-S—, cycloalkyl-S—, aryl-S—, heteroaryl-S—, and heterocyclyl-S—, where alkyl, cycloalkyl, aryl, heteroaryl and heterocyclyl are as described herein.

"Thioacyl" refers to groups H—C(S)—, alkyl-C(S)—, cycloalkyl-C(S)—, aryl-C(S)—, heteroaryl-C(S)—, and heterocyclyl-C(S)—, where alkyl, cycloalkyl, aryl, heteroaryl and heterocyclyl are as described herein.

"Oxythioacyl" refers to groups HO—C(S)—, alkylO—C(S)—, cycloalkylO—C(S)—, arylO—C(S)—, heteroarylO—C(S)—, and heterocyclylO—C(S)—, where alkyl, cycloalkyl, aryl, heteroaryl and heterocyclyl are as described herein.

"Oxythioacyloxy" refers to groups HO—C(S)—O—, alkylO—C(S)—O—, cycloalkylO—C(S)—O—, arylO—C(S)—O—, heteroarylO—C(S)—O—, and heterocyclylO—C(S)—O—, where alkyl, cycloalkyl, aryl, heteroaryl and heterocyclyl are as described herein.

"Phosphorylamino" refers to the groups —NR*—P(O)(R)(OR*) where R* represents H, alkyl, cycloalkyl, alkenyl, or aryl, R represents OR* or is hydroxy or amino and R*** is alkyl, cycloalkyl, aryl or arylalkyl, where alkyl, amino, alkenyl, aryl, cycloalkyl, and arylalkyl are as described herein.

"Thioacyloxy" refers to groups H—C(S)—O—, cycloalkyl-C(S)—O—, aryl-C(S)—O—, heteroaryl-C(S)—O—, and heterocyclyl-C(S)—O—, where alkyl, cycloalkyl, aryl, heteroaryl, and heterocyclyl are as described herein.

"Sulfinyl" refers to groups H—S(O)—, alkyl-S(O)—, cycloalkyl-S(O)—, aryl-S(O)—, heteroaryl-S(O)—, and heterocyclyl-S(O)—, where alkyl, cycloalkyl, aryl, heteroaryl and heterocyclyl are as described herein.

"Sulfonyl" refers to groups H—S(O)$_2$—, alkyl-S(O)$_2$—, cycloalkyl-S(O)$_2$—, aryl-S(O)$_2$—, heteroaryl-S(O)$_2$—, and heterocyclyl-S(O)$_2$—, where alkyl, cycloalkyl, aryl, heteroaryl and heterocyclyl are as described herein.

"Sulfinylamino" refers to groups H—S(O)—NR*—, alkyl-S(O)—NR*—, cycloalkyl-S(O)—NR*—, aryl-S(O)—NR*—, heteroaryl-S(O)—NR*—, and heterocyclyl-S(O)—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Sulfonylamino" refers to groups H—S(O)$_2$—NR*—, alkyl-S(O)$_2$—NR*—, cycloalkyl-S(O)$_2$—NR*—, aryl-S(O)$_2$ —NR*—, heteroaryl-S(O)$_2$—NR*—, and heterocyclyl-S(O)$_2$—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfinylamino" refers to groups HO—S(O)—NR*—, alkylO—S(O)—NR*—, cycloalkylO—S(O)—NR*—, arylO—S(O)—NR*—, heteroarylO—S(O)—NR*—, and heterocyclylO—S(O)—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfonylamino" refers to groups HO—S(O)$_2$—NR*—, alkylO—S(O)$_2$—NR*—, cycloalkylO—S(O)$_2$—NR*—, arylO—S(O)$_2$—NR*—, heteroarylO—S (O)$_2$—NR*—, and heterocyclylO—S(O)$_2$—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Aminothioacyl" refers to groups R*R*N—C(S)—, where each R* is independently hydrogen, alkyl, cycloalkyl, aryl, heteroaryl, and heterocyclic and where each of alkyl, cycloalkyl, aryl, heteroaryl and heterocyclyl is as described herein.

"Thioacylamino" refers to groups H—C(S)—NR*—, alkyl-C(S)—NR*—, cycloalkyl-C(S)—NR*—, aryl-C(S)—NR*—, heteroaryl-C(S)—NR*—, and heterocyclyl-C(S)—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Aminosulfinyl" refers to groups R*R*N—S(O)—, where each R* is independently hydrogen, alkyl, cycloalkyl, aryl, heteroaryl, and heterocyclic and where each of alkyl, cycloalkyl, aryl, heteroaryl and heterocyclyl is as described herein.

"Aminosulfonyl" refers to groups R*R*N—S(O)$_2$—, where each R* is independently hydrogen, alkyl, cycloalkyl, aryl, heteroaryl, and heterocyclic and where each of alkyl, cycloalkyl, aryl, heteroaryl and heterocyclyl is as described herein.

In this specification "optionally substituted" is taken to mean that a group may or may not be further substituted or fused (so as to form a condensed polycyclic group) with one or more groups selected from hydroxy, acyl, alkyl, alkoxy, alkenyl, alkenyloxy, alkynyl, alkynyloxy, amino, aminoacyl, thio, arylalkyl, arylalkoxy, aryl, aryloxy, acylamino, cyano, halogen, nitro, sulfo, phosphono, phosphorylamino, phosphinyl, heteroaryl, heteroaryloxy, heterocyclyl, heterocyclyloxy, oxyacyl, oxime, oxime ether, hydrazone, —NHC(NH)NH$_2$, oxyacylamino, oxysulfonylamino, aminoacyloxy, trihalomethyl, trialkylsilyl, pentafluoroethyl, trifluoromethoxy, difluoromethoxy, trifluoromethanethio, trifluoroethenyl, mono- and di-alkylamino, mono- and di-(substituted alkyl)amino, mono- and di-arylamino, mono- and di-heteroarylamino, mono- and di-heterocyclyl amino, and unsymmetric di-substituted amines having different substituents selected from alkyl, aryl, heteroaryl and heterocyclyl, and the like.

An optionally substituted amino group may also include amino acid and peptide residues.

The TPI compounds of formula I, Ia, Ib, or II may be prepared by known methods including those disclosed in WO 02/060872 and WO 07/087,684 which are incorporated herein by reference.

In a further preferred embodiment the TPI for use in the present combination therapy is a compound of formula (III) or a salt, solvate or prodrug thereof

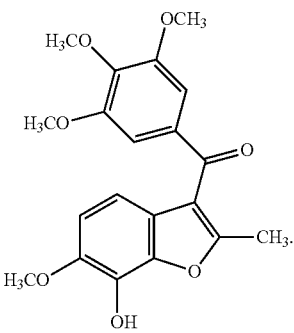 [SMILES: COc1cc(C(=O)c2c(C)oc3c(O)c(OC)ccc23)cc(OC)c1OC]

The compound of formula (III) (2-Methyl-7-hydroxy-3-(3,4,5-trimethoxybenzoyl)-6-methoxybenzofuran) can be prepared by the synthetic methodology described in PCT/AU2007/000101 (WO 07/087,684).

The compounds of formula I, Ia, Ib, II or III have been observed to be potent tubulin polymerisation inhibitors (TPIs). An important aspect of the compounds of formulae I, Ia, Ib, II and III is the combination of the specific C-6 and C-7 substituents together with the C-2 Q-group (especially C-2 methyl) which appears to confer greater potency and selectivity when compared to other structurally related TPI compounds. In these compounds selectivity is not simply reliant on the predisposition of tumour vasculature towards collapse when challenged with the VDA but on a capacity of the VDA to distinguish between tumour endothelial cells and normal endothelial cells. Normal endothelial cells, found in healthy tissues, are in a "quiescent" state and tumour endothelial cells are in an "activated" state. Most VDAs do not distinguish between these two states, for example, Combretastatin A4 (CA4) is equally potent against quiescent and activated endothelial cells. However, the compounds of formulae I, Ia, Ib, II and particularly III show selectivity towards tumor endothelial cells (activated) over normal endothelial cells (quiescent).

It will be appreciated that the TPIs of the invention and compounds of formula I, Ia, Ib, II, or III can be administered to a subject as a pharmaceutically acceptable salt thereof. Suitable pharmaceutically acceptable salts include, but are not limited to salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benzenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium. In particular, the present invention includes within its scope cationic salts eg sodium or potassium salts, or alkyl esters (eg methyl, ethyl) of the phosphate group.

It will also be appreciated that any compound that is a prodrug of a TPI of the invention or a compound of formula I, Ia, Ib, II, and III are also within the scope and spirit of the invention. The term "pro-drug" is used in its broadest sense and encompasses those derivatives that are converted in vivo to a compound of the invention (for instance, a compound of formulae I, Ia, Ib, II, and III). Such derivatives would readily occur to those skilled in the art, and include, for example, compounds where the free hydroxy group (for instance at C-7 position or $R^{1D}$) is converted into an ester, such as an acetate or phosphate ester, or where a free amino group (for instance at C-7 position or $R^{1D}$) is converted into an amide (e.g., α-aminoacid amide). Procedures for esterifying, eg. acylating, the compounds are well known in the art and may include treatment of the compound with an appropriate carboxylic acid, anhydride or chloride in the presence of a suitable catalyst or base. A particularly preferred prodrug is a disodium phosphate ester. The disodium phosphate ester (in particular a C-7 disodium phosphate ester of a compound of formula III) of the compound of the invention may be useful in increasing the solubility of the compounds. This would, for instance, may allow for delivery of the compound in a benign vehicle like saline. The disodium phosphate ester may be prepared in accordance with the methodology described in Pettit, G. R., et al, *Anticancer Drug Des.*, 1995, 10, 299. Other texts which generally describe prodrugs (and the preparation thereof) include: *Design of Prodrugs*, 1985, H. Bundgaard (Elsevier); *The Practice of Medicinal Chemistry*, 1996, Camille G. Wermuth et al., Chapter 31 (Academic Press); and *A Textbook of Drug Design and Development*, 1991, Bundgaard et al., Chapter 5, (Harwood Academic Publishers).

The compounds of formulae I, Ia, Ib, II, and III (or a salt or prodrug thereof) may be in crystalline form either as the free compound or as a solvate (e.g. hydrate) and it is intended that both forms are within the scope of the present invention. Methods of solvation are generally known within the art.

Combination Partner (b); mTOR Inhibitor mTOR is an intracellular serine/threonine kinase primarily involved in the control of translational initiation. PI3K/Akt-dependent phosphorylation signals through tuberin, the protein product of the TSC1/TSC2 complex, leading to mTOR activation. mTOR subsequently phosphorylates downstream targets, causing initiation of protein translation.

Accordingly, any agent that inhibits the activation of mTOR, causing downregulation of its downstream targets, is encompassed by the meaning of "mTOR inhibitor" as used herein.

Suitable mTOR inhibitors include:
BEZ235 (NVP-BEZ235), deforolimus (AP 23573, MK-8669), PI-103, rapamycin (Sirolimus, Rapamune), temsirolimus (Toricel, CCI-779), everolimus (Afinitor, RAD001, Certican), ABT 578, SAR 543 and AP 23841.

The suitability of any mTOR combination partner will often depend on the mode of delivery. Temsirolimus and Everolimus (which are both analogues of rapamycin) have been developed with superior solubility properties compared to rapamycin that make them suitable for intravenous dosing (temsirolimus) and oral dosing (everolimus).

Proliferative Diseases

As used herein the term "proliferative disease" broadly encompasses any neoplastic disease including those which are potentially malignant (pre-cancerous) or malignant (cancerous). The term therefore encompasses the treatment of tumours.

Accordingly, the term "tumour" is used generally to define any malignant cancerous or pre-cancerous cell growth, and may include leukemias and carcinomas such as melanomas, colon, lung, ovarian, skin, breast, pancreas, pharynx, brain prostate, CNS, and renal cancers, as well as other cancers.

In a preferred embodiment the combination may be used in the treatment of tumours and in particular in the following tumours: breast adenocarcinoma, brain glioblastoma, colorectal adenocarcinoma, lung carcinoma, ovary adenocarcinoma, pancreatic adenocarcinoma, prostate carcinoma, renal cell adenocarcinoma, and pharynx squamous cell carcinoma.

In a preferred aspect the invention provides a combination of (a) and (b) for the treatment of renal cancer, and in particular metastatic renal cell carcinoma.

The Combination of (a) and (b)

Without wishing to be bound to any particular theory it is believed that partners (a) and (b) work in combination to better effect cancer cell death. As illustrated in FIG. 1 it is postulated that the TPI induces hypoxia/cytotoxic stress in highly vascular tumours while mTOR inhibition concomitantly suppresses HIF1a driven angiogenic/survival responses to yield a beneficial additive or synergistic effect.

The present invention therefore provides a method of treating tumours comprising the administration of an effective amount of (a) a tubulin targeting agent in combination with an effective amount of (b) a mTOR inhibitor.

In embodiments the following combinations are particularly preferred:

| Combination partner (a) | + | Combination partner (b) | = | treatment |
|---|---|---|---|---|
| Compounds of formula III (or prodrug thereof) | + | temsirolimus | | renal cancer |
| Compounds of formula III (or prodrug thereof) | + | rapamycin | | renal cancer |
| Compounds of formula III (or prodrug thereof) | + | everolimus | | renal cancer |
| Compounds of formula III (or prodrug thereof) | + | sirolimus | | renal cancer |
| Compounds of formula III (or prodrug thereof) | + | deforolimus | | renal cancer |
| Compounds of formula III (or prodrug thereof) | + | temsirolimus | | ovarian cancer |
| Compounds of formula III (or prodrug thereof) | + | rapamycin | | ovarian cancer |
| Compounds of formula III (or prodrug thereof) | + | everolimus | | ovarian cancer |
| Compounds of formula III (or prodrug thereof) | + | sirolimus | | ovarian cancer |
| Compounds of formula III (or prodrug thereof) | + | deforolimus | | ovarian cancer |
| Compounds of formula III (or prodrug thereof) | + | temsirolimus | | lung cancer |
| Compounds of formula III (or prodrug thereof) | + | rapamycin | | lung cancer |
| Compounds of formula III (or prodrug thereof) | + | everolimus | | lung cancer |
| Compounds of formula III (or prodrug thereof) | + | sirolimus | | lung cancer |
| Compounds of formula III (or prodrug thereof) | + | deforolimus | | lung cancer |

In the above embodiments preferably the prodrug form is the C-7 disodium phosphate ester of a compound of formula III.

An "effective amount" is intended to mean that the amount of each combination partner, when administered to a mammal (in particular a human) in need of such treatment, is sufficient to effect treatment for a particular proliferative disease. Thus, for example, a therapeutically effective amount of a compound of combination partner (a) (or a pharmaceutically acceptable salt, solvate, or prodrug thereof) is a quantity sufficient to synergise or potentiate the activity of the mTOR inhibitor (or vice versa) such that a targeted disease is reduced or alleviated.

This may include at least partially attaining the desired effect, or delaying the onset of, or inhibiting the progression of, or halting or reversing altogether the onset or progression of the particular disease (e.g., tumour) being treated.

Clinical studies such as open-label, dose escalation studies in patients with proliferative diseases may include studies to prove the synergism of the active ingredients of the combination. The beneficial and/or synergistic effects can be determined directly through the results of these studies which are known as such to a person skilled in the art. These studies are also able to compare the effects of a monotherapy using the active ingredients and a combination of the invention. Preferably, the dose of combination partner (a) may be escalated until the Maximum Tolerated Dosage (MTD) is reached, and agent (b) is administered as a fixed dose. Alternatively, combination partner (a) is administered in a fixed dose and the dose of agent (b) is escalated. Each patient may receive doses of agent (a) either daily or intermittent. The efficacy of the treatment can be determined in such studies, e.g., after 6, 12, 18 or 24 weeks by evaluation of symptom scores every 9 weeks.

The administration of the pharmaceutical combination of the present invention may result not only in a beneficial effect, e.g., an additive or synergistic therapeutic effect, for instance, with regard to alleviating, delaying progression of or inhibiting the symptoms, but also in further surprising beneficial effects. Such other effects may include fewer side effects, an improved quality of life or a decreased morbidity, compared with a monotherapy applying only one of the pharmaceutically active ingredients used in the combination of the present invention.

A further benefit of the invention is that lower doses of the active ingredients of the combination can be used. The dosages need not only be smaller but may also be applied less frequently, which may diminish the incidence or severity of side effects.

The term "administration" relates to the co-administration of the combination partners to a single patient, and are intended to include treatment regimens in which the agents are not necessarily administered by the same route of administration or at the same time. Accordingly, combination partners (a) and (b) may be administered together, one after the other or separately in one combined unit dosage form or in two separate unit dosage forms. The unit dosage form may also be a fixed combination such as a pharmaceutical composition which comprises both partner (a) (or a salt, solvate or prodrug thereof) and partner (b).

In particular, a therapeutically effective amount of each of the combination partner of the combination of the invention may be administered simultaneously or sequentially and in any order, and the components may be administered separately or as a fixed combination. For example, the method of preventing or treating proliferative diseases according to the invention may comprise: (i) administration of partner (a) in free or pharmaceutically acceptable salt form; and (ii) administration of partner (b) in free or pharmaceutically acceptable salt form, simultaneously or sequentially in any order, in jointly therapeutically effective amounts, preferably in synergistically effective amounts, e.g., in daily or intermittent dosages corresponding to the amounts described herein. The individual combination partners of the combination of the invention may be administered separately at different times during the course of therapy or concurrently in divided or single combination forms. Furthermore, the term administering also encompasses the use of a pro-drug of a combination partner that converts in vivo to the combination partner as such. The present invention is therefore to be understood as embracing all such regimens of simultaneous or alternating treatment and the term "administering" is to be interpreted accordingly.

As such it will be appreciated that the combination, partners may be presented as a "kit of parts" for use in the treatment of a proliferative disease (e.g., tumour therapy). The kit may comprise a package where the combination partners are supplied separately for co-administration with instructions for use in the particular therapy.

The effective dosage of each of the combination partners employed in the combination of the invention may vary depending on the particular compound or pharmaceutical composition employed, the mode of administration, the condition being treated, the severity of the condition being treated. Thus, the dosage regimen of the combination of the invention is selected in accordance with a variety of factors including the route of administration and the renal and hepatic function of the patient. A physician of ordinary skill can readily determine and prescribe the effective amount of the single active ingredients required to alleviate, counter or arrest the progress of the condition.

Daily dosages for combination partners (a) and (b) will, of course, vary depending on a variety of factors, e.g., the compound chosen, the particular condition to be treated and the desired effect. In general, however, satisfactory results are achieved on administration of agent (a) at daily dosage rates of about 0.05 to 20 mg/kg per day, particularly 1 to 20 mg/kg per day, e.g. 0.4 to 16 mg/kg per day, as a single dose or in divided doses. Combination partner (a) and partner (b) may be administered by any conventional route, in particular enterally, e.g., orally, e.g., in the form of tablets, capsules, drink solutions or parenterally, e.g., in the form of injectable solutions or suspensions. Suitable unit dosage forms for oral administration comprise from about 0.02 to 50 mg active ingredient, usually 0.1 to 30 mg and 2 to 25 mg, 4 to 20 mg e.g. combination partner (a) or (b), together with one or more pharmaceutically acceptable diluents or carriers therefore.

Combination partner (b) may be administered to a human in a daily dosage range of 0.5 to 1000 mg. Suitable unit dosage forms for oral administration comprise from about 0.1 to 500 mg active ingredient, preferably 5-50 mg/day, more preferably 5-20 mg/day, and most preferably about 7-12 mg/day, together with one or more pharmaceutically acceptable diluents or carriers therefore. Methods and administration regimes for delivery known mTOR inhibitors would be known to the skilled clinician.

For instance, an administration regime may include adding the TPI (e.g., compound of formula III) at an assigned dose level by I.V. on days 1 and 8 (of a 21 day cycle) where the mTOR inhibitor is given as an oral daily dose (e.g., about 10 mg/day). In this embodiment the compound of formula (III) may be dosed at a level of between 4 to 16 mg/m$^2$.

The administration of a pharmaceutical combination of the invention results not only in a beneficial effect, e.g., an additive or synergistic therapeutic effect, e.g., with regard to inhibiting the growth of tumors, but also in further surprising beneficial effects, e.g., less side effects, an improved quality of life or a decreased morbidity, compared to a monotherapy applying only one of the pharmaceutically active ingredients used in the combination of the invention.

A further benefit is that lower doses of the active ingredients of the combination of the invention can be used, e.g., that the dosages need not only often be smaller but are also applied less frequently, or can be used in order to diminish the incidence of side effects. This is in accordance with the desires and requirements of the patients to be treated.

Combinations of partners (a) and (b) may be combined, independently or together, with one or more pharmaceutically acceptable carriers and, optionally, one or more other conventional pharmaceutical adjuvants and administered enterally, e.g., orally, in the form of tablets, capsules, caplets, etc. or parenterally, e.g., intraperitoneally or intravenously, in the form of sterile injectable solutions or suspensions. The enteral and parenteral compositions may be prepared by conventional means.

The pharmaceutical compositions for separate administration of combination partner (a) and partner (b) or for the administration in a fixed combination (i.e., a composition), according to the invention may be prepared in a manner known in the art and are those suitable for enteral, such as oral or rectal, and parenteral administration to mammals (warm-blooded animals), particularly humans, comprising a therapeutically effective amount of at least one pharmacologically active combination partner alone, e.g., as indicated above, or in combination with one or more pharmaceutically acceptable carriers or diluents, especially suitable for enteral or parenteral application.

Suitable pharmaceutical compositions contain, e.g., from about 0.1% to about 99.9%, preferably from about 1% to about 60%, of the active ingredient(s).

The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal patches may also be used to administer the compounds of the invention.

Compositions for rectal administration may be presented as a suppository with a suitable base comprising, for example, cocoa butter, glycerin, gelatine or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols; zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLES

Synthetic Protocols

Preparation of 2-Bromo-7-acetoxy-3-(3,4,5-trimethoxybenzoyl)-6-methoxybenzofuran

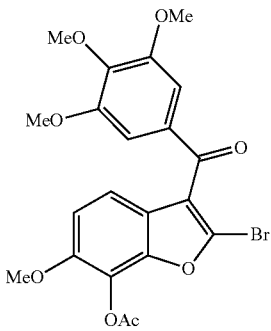 [SMILES: COc1cc(C(=O)c2c(Br)oc3c(OC(C)=O)c(OC)ccc23)cc(OC)c1OC]

Step 1: 2-t-Butyldimethylsilyl-3-(t-butyldimethylsilyloxymethylene)-6-methoxy-7-isopropoxybenzofuran (Larock coupling)

A suspension of 2-isopropoxy-3-methoxy-5-iodophenol (4.41 mmol), 1-(tert-butyldimethylsilyl)-3-(tert-butyldimethylsilyloxy)propyne (1.5 g, 5.28 mmol), lithium chloride (189 mg, 4.45 mmol) and sodium carbonate (2.34 g, 22.08 mmol) in dry dimethylformamide (5 mL) at 100° C. was deoxygenated 4 times by evacuation and backfilling with nitrogen. Palladium acetate (135 mg, 0.60 mmol) was added and the reaction vessel was degassed twice with nitrogen. The reaction mixture was then stirred at this temperature for 4 hours (tlc) and the solvent was removed by distillation under vacuum. The residue was dissolved in ethyl acetate (75 mL), stirred well, filtered and treated with triethylamine (5 mL). The solution was concentrated onto silica gel (10 g) and purified by flash chromatography (silica gel, eluent=hexane/ diethyl ether/triethylamine; 95:5:1%) to afforded the title compound as a yellow oil (1.45 g, 96%); $^1$H NMR (300 MHz, CDCl$_3$) δ 7.24(d, 1H, J=8.45 Hz), 6.88(d, 1H, J=8.47 Hz), 4.80(s, 2H, CH$_2$), 4.73(m, 1H), 3.88(s, 3H, OMe), 1.36(d, 6H, J=6.17 Hz), 0.94(s, 9H), 0.92(s, 9H), 0.35(s, 6H), 0.12(s, 6H).

Step 2: 2-t-Butyldimethylsilyl-3-formyl-6-methoxy-7-isopropoxybenzofuran

To a solution of 2-t-butyldimethylsilyl-3-(t-butyldimethylsilyloxymethylene)-6-methoxy-7-isopropoxybenzofuran (2.69 mmol) in methanol (100 mL) was added concentrated hydrochloric acid (200 µL) and the reaction was stirred for 30 minutes (monitored by tlc), quenched with triethylamine (2 mL) and the solvent removed by distillation under vacuum. The residue was dissolved in dichloromethane (20 mL), washed with water (10 mL), dried over magnesium sulfate, concentrated under vacuum and co-distilled with toluene (20 mL). The crude product was dissolved in dry dichloromethane (4 mL) and added to a stirred solution of Collin's reagent (chromium trioxide (1.01 g), pyridine (1.65 mL) in dry dichloromethane (30 mL)). The suspension was stirred for 10 minutes, filtered and the residue washed with diethyl ether (20 mL). The filtrate was concentrated onto silica (10 g) and purified by flash chromatography (silica gel, eluent=hexane/diethyl-ether/triethylamine (90:9:1) to afford the title compound as a light yellow oil (503 mg, 48%); $^1$H NMR (300 MHz, CDCl$_3$) δ 10.25(s, 1H, CHO), 7.79(d, 1H, J=8.45 Hz), 6.98(d, 1H, J=8.46 Hz), 4.65(m, 1H), 3.89(s, 3H, OMe), 1.35(d, 6H, J=6.17 Hz), 0.97(s, 9H), 0.45(s, 6H).

Step 3: 2-t-Butyldimethylsilyl-3-(3,4,5-trimethoxybenzoyl)-6-methoxy-7-isopropoxybenzofuran To a stirred solution of 3,4,5-trimethoxyiodobenzene (377 mg, 1.27 mmol) in dry tetrahydrofuran (1 mL) at −78° C. under nitrogen was added n-butyllithium (795 µL, 1.59 mmol, 2M solution in cyclohexane) and the reaction mixture was stirred at this temperature for 40 minutes. After this time a solution of 2-t-butyldimethylsilyl-3-formyl-6-methoxy-7-isoproxybenzofuran (1.07 mmol) in dry tetrahydrofuran (1 mL) was added to the reaction dropwise via syringe pipette. The reaction mixture was stirred at −60° C. for 20 minutes and then allowed to warm to 0° C., stirred for 10 minutes, quenched with saturated ammonium chloride solution (2 mL) and diluted with ethyl acetate (20 mL). The organic layer was washed with water (10 mL), dried over magnesium sulfate and the solvent was removed under vacuum to give a residue that was co-distilled with toluene. The crude product (908 mg) was dissolved in dry tetrahydrofuran (10 mL) and treated with 2,3-dichloro-5,6-dicyano-1,4-benzoquinone (900 mg, 1.59 mmol) was added. The reaction mixture was stirred at room temperature for 16 hours (monitored by tlc) and then loaded onto silica (10 g) and purified by flash chromatography (silica gel, eluent=hexane/diethyl ether/triethylamine, 90:9:1) to afford the title compound as a light yellow oil (498 mg, 69%); $^1$H NMR (300 MHz, CDCl$_3$) δ 7.14(s, 2H, benzoyl Hs), 6.81(d, 1H, J=8.64 Hz), 6.77(d, 1H, J=8.64 Hz) 4.74(m, 1H), 3.93(s, 3H, OMe), 3.86(s, 3H, OMe), 3.78(s, 6H, 2×OMe), 1.39(d, 6H, J=6.14 Hz), 1.01(s, 9H), 0.26(s, 6H).

Step 4: 2-(tert-butyldimethylsilyloxy)-7-acetoxy-3-(3,4,5-trimethoxybenzoyl)-6-methoxybenzofuran To a stirred solution of 2-(t-butyldimethylsilyloxy)-7-isopropoxy-3-(3,4,5-trimethoxybenzoyl)-6-methoxy-benzofuran (160 mg, 0.31 mmol) in dry DCM (2 mL) at room temperature under nitrogen was added solid aluminium trichloride (83 mg, 0.62 mmol) and the reaction mixture was stirred for 15 minutes (monitored by tlc). The reaction was quenched with a saturated solution of ammonium chloride, extracted with dichloromethane and dried over magnesium sulfate. The solvent was removed by distillation and residue was dried by azeotropic removal of water with toluene. The crude product was dissolved in pyridine (2 mL), acetic anhydride (1 mL) was added and reaction mixture was stirred for 2 hours at room temperature. The solvent was distilled under vacuum and the residue was loaded onto silica gel (1 g) and purified by column chromatography (silica gel, eluent, hexane:diethyl-ether; 80:20) (134 mg, 84%); $^1$H NMR (300 MHz, CDCl$_3$) δ 7.14(s, 2H, benzoyl Hs), 6.98(d, 1H, J=8.72

Hz), 6.85(d, 1H, J=8.72 Hz), 3.93(s, 3H, OMe), 3.86(s, 3H, OMe), 3.80(s, 6H, 2×OMe), 2.41(s, 3H), 0.99(s, 9H), 0.25(s, 6H).

Step 5: 2-Bromo-7-acetoxy-3-(3,4,5-trimethoxybenzoyl)-6-methoxybenzofuran

To a stirred solution of 2-t-butyldimethylsilyl-7-acetoxy-3-(3,4,5-trimethoxybenzoyl)-6-methoxybenzofuran (120 mg, 0.44 mmol) in 1,2-dichloroethane (1 mL) at room temperature under nitrogen was added bromine (12 μl, 0.44 mmol) dropwise and the reaction mixture was stirred at this temperature for 10 minutes. After this time the reaction was quenched with saturated sodium thiosulfate solution, extracted with ethyl acetate (20 mL), dried over magnesium sulfate and the solvent removed by distillation under vacuum. The crude product was purified by silica gel column chromatography (eluent=Hexane:diethyl ether; 8:2-7:3) to afford the title compound as a colourless crystalline solid (91 mg, 81%); $^1$H NMR (300 MHz, CDCl$_3$) δ 7.40(d, 1H, J=8.70 Hz), 7.14 (s, 2H, benzoyl-Hs), 6.98(d, 1H, J=8.75 Hz), 3.94(s, 3H, OMe), 3.89(s, 3H, OMe), 3.86(s, 6H, 2×OMe), 2.43(s, 3H); $^{13}$C NMR (75 MHz, CDCl$_3$) δ 187.95(CO), 167.71, 152.75, 149.54, 147.49, 142.59, 131.92, 131.80, 123.91, 121.84, 119.89, 117.72, 109.89, 106.92, 60.69, 56.61, 56.00, 20.09.

Example 1

Preparation of 2-Methyl-7-hydroxy-3-(3,4,5-trimethoxybenzoyl)-6-methoxybenzofuran

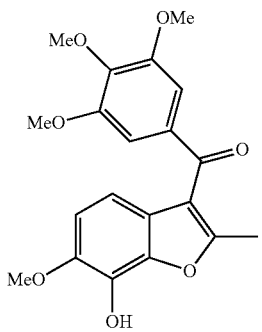 [SMILES: COc1cc(C(=O)c2c(C)oc3c(O)c(OC)ccc23)cc(OC)c1OC]

Preparation A

To a stirred solution of 2-Bromo-7-acetoxy-3-(3,4,5-trimethoxybenzoyl)-6-methoxybenzofuran (20 mg, 0.042 mmol), methyl-boronic acid (40 mg, 0.67 mmol), in 1,4-dioxane (2 mL) at 90° C. was added tetrakis-triphenylphosphine palladium (11 mg, 0.01 mmol) followed by the addition of a solution of sodium bicarbonate (40 mg, 0.48 mmol) in distilled water (0.5 mL). The reaction mixture turned red after 5 minutes. After 2 hours (tlc) the reaction mixture was brought to room temperature and was added saturated ammonium chloride (2 mL) and diluted with dichloromethane (20 mL). The organic layer was separated and washed with water, dried over magnesium sulfate and the solvent was removed by distillation under vacuum. The residue was purified by PTLC (eluent=Dichloromethane/Methanol, 1:1) to give the title compound (acetate cleaved during reaction) as a fluffy white solid; (3 mg, 19%).

Preparation B (Negishi Coupling)

To a stirred solution of zinc-bromide (592 mg, 2.63 mmol) in dry THF (1.5 mL) at 0° C. was added the solution of methyl lithium (1.6 M solution in diethyl-ether, 2.6 mL, 4.15 mmol) and the reaction mixture was stirred for 2 hours. Solid 2-bromo-7-acetoxy-3-(3,4,5-trimethoxybenzoyl)-6-methoxy-benzofuran (300 mg, 0.63 mmol) was added and the ether was removed under vacuum and to the rest suspension was added dichlorobis(triphenylphosphine)palladium catalyst (21 mg) and catalytic amount of copper (I) iodide. The reaction mixture was stirred at room temperature for 36 hours (monitored by tlc), quenched with saturated ammonium chloride solution and extracted with dichloromethane (10 mL), dried over magnesium sulfate and solvent distilled under vacuum and the product was purified by silica gel column (eluent=hexane/ethyl acetate; 8:2). The product was crystallized in methanol (106 mg, 46%); NMR (300 MHz, CDCl$_3$) δ 7.09(s, 2H, benzoyl Hs), 6.93(d, 1H, J=8.54 Hz), 6.83(d, 1H, J=8.56 Hz), 5.70(bs, 1H, OH), 3.93(s, 3H, OMe), 3.92(s, 3H, OMe), 3.83(s, 6H, 2×OMe), 2.54(s, 3H, 2-Me)

Example 2

Preparation of Disodium 6-methoxy-2-methyl-3-(3,4,5-trimethoxybenzoyl)benzofuran-7-yl phosphate

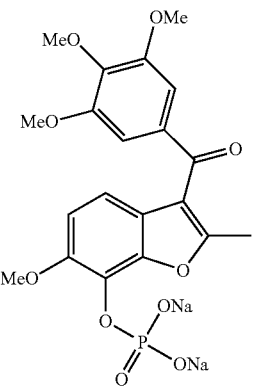

Step 1: Dibenzyl 6-methoxy-2-methyl-3-(3,4,5-trimethoxybenzoyl)benzofuran-7-yl phosphate To a mixture of 0.081 g (0.22 mmol) of (7-hydroxy-6-methoxy-2-methylbenzofuran-3-yl)(3,4,5-trimethoxyphenyl)methanone, 0.086 g (0.261 mmol) of carbon tetrabromide and 0.063 ml (0.283 mmol) of dibenzylphosphite in 2.5 ml of anhydrous acetonitrile 0.046 ml of anhydrous triethylamine was added dropwise at 0° C. under nitrogen atmosphere. The resulting mixture was stirred for 2 h at room temperature, then diluted to 20 ml with ethyl acetate, washed with water brine, dried over anhydrous magnesium sulfate, filtered off and evaporated to dryness under reduced pressure. The residue was purified by flash column chromatography (dichloromethane/ethyl acetate, 9:1) to give the title compound as a colorless foam (0.13 g, 94%); $^1$H NMR (CDCl$_3$) δ 2.42 (s, 3H, Me-2); 3.83 (s, 1H, OMe); 3.93 (s, 3H, OMe); 5.33 (m, 4H, CH$_2$Ph); 6.89 (d, CH aromatic, J=8.7 Hz); 7.21 (dd, 1H, CH aromatic, J=8.72 Hz; J=1.2 Hz); 7.08 (s, 2H, CH aromatic); 7.29-7.43 (m, 10H, CH aromatic).

Step 2: Disodium 6-methoxy-2-methyl-3-(3,4,5-trimethoxybenzoyl)benzofuran-7-yl phosphate To a stirred solution of 0.122 g (0.193 mmol) of the product from Step 1 in 1 ml of anhydrous acetonitrile 0.075 ml (0.58 mmol) of bromotrimethylsilane was added at −5° C. under nitrogen atmosphere. The resulting mixture was stirred for 1 h at 0° C., then evaporated to dryness in vacuo. The residue was diluted to 5 ml with anhydrous methanol and pH of the solution was brought up about 10 by the addition of sodium methoxide. After evaporation of the resulting mixture under reduced pressure the solid residue was washed with anhydrous isopropanol (4×1.5 ml) and anhydrous ethanol (3×1.5 ml) and dried under vacuum to give 0.062 g (65% yield) of title compound as an colorless solid; $^1$H NMR (D$_2$O) δ 2.37 (s, 3H, Me-2); 3.76 (s, 6H, OMe); 3.79 (s, 3H, OMe); 3.82 (s, 3H, OMe); 4.66 (s, H$_2$O); 6.93 (d, 1H, CH aromatic, J=8.6 Hz); 7.04 (d, 1H, CH aromatic, J=8.6 Hz); 7.10 (s, 2H, CH aromatic).

Biological Data (A) (i) In Vitro Studies for Combination Partner (a)

TABLE 1

In Vitro Data for Compounds: These are the results for growth inhibition studies of compounds using the Sulforhodamine B (SRB) or Systmex cell counting (CC) assays. IC$_{50}$ is the concentration required to inhibit net cell growth by 50%.

| Example | Structure | Cancer cell line[a]: IC$_{50}$, nM | HUVECs[c] Tum: IC$_{50}$, nM Norm: IC$_{50}$, nM |
|---|---|---|---|
| 3 | (structure) | 5 | Tum: 1-10<br>Norm: 1-10 |
| 4 | (structure) | 5 | Tum: 1-10<br>Norm: 1-10 |
| 5 | (structure) | 55 | Tum: 10-100<br>Norm: 10-100 |
| 6 | (structure) | 500 | Tum: 100-1000<br>Norm: 100-1000 |

TABLE 1-continued

In Vitro Data for Compounds: These are the results for growth inhibition studies of compounds using the Sulforhodamine B (SRB) or Systmex cell counting (CC) assays. $IC_{50}$ is the concentration required to inhibit net cell growth by 50%.

| Example | Structure | Cancer cell line[a]: $IC_{50}$, nM | HUVECs[c] Tum: $IC_{50}$, nM Norm: $IC_{50}$, nM |
|---|---|---|---|
| 7 | (structure) | 45 | Tum: 10-100<br>Norm: 10-100 |
| 8 | (structure) | 35 | Tum: 100-1000<br>Norm: 100-1000 |
| 9 | (structure) | 800 | Tum: >1000<br>Norm: >1000 |
| 10 | (structure) | 3.5 | Tum: 1-10<br>Norm: 0.1-1 |

TABLE 1-continued

In Vitro Data for Compounds: These are the results for growth inhibition studies of compounds using the Sulforhodamine B (SRB) or Systmex cell counting (CC) assays. $IC_{50}$ is the concentration required to inhibit net cell growth by 50%.

| Example | Structure | Cancer cell line[a]: $IC_{50}$, nM | HUVECs[c] Tum: $IC_{50}$, nM Norm: $IC_{50}$, nM |
|---|---|---|---|
| 11 | (structure) | 1.2 | Tum: 0.1-1 Norm: 1-10 |
| 12 | (structure) | 3.3 | Tum: 1-10 Norm: 1-10 |
| 13 | (structure) | 35 | Tum: 1-10 Norm: 10-100 |
| 14 | (structure) | 2.0 | Tum: 0.1-1 Norm: 10-100 |

TABLE 1-continued

In Vitro Data for Compounds: These are the results for growth inhibition studies of compounds using the Sulforhodamine B (SRB) or Systmex cell counting (CC) assays. $IC_{50}$ is the concentration required to inhibit net cell growth by 50%.

| Example | Structure | Cancer cell line[a]: $IC_{50}$, nM | HUVECs[c] Tum: $IC_{50}$, nM Norm: $IC_{50}$, nM |
|---|---|---|---|
| 15 | 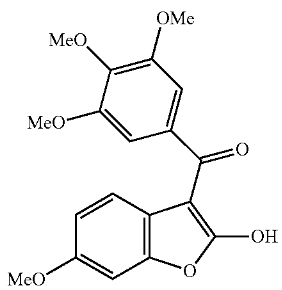 [SMILES: COc1ccc2c(C(=O)c3cc(OC)c(OC)c(OC)c3)c(O)oc2c1] | 575 | Tum: 100-1000  Norm: 100-1000 |
| 16 | 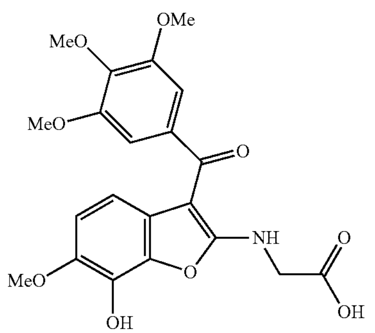 [SMILES: COc1cc(C(=O)c2c(NCC(=O)O)oc3c(O)c(OC)ccc23)cc(OC)c1OC] | 260 | Tum: 100-1000  Norm: 100-1000 |
| 17 | 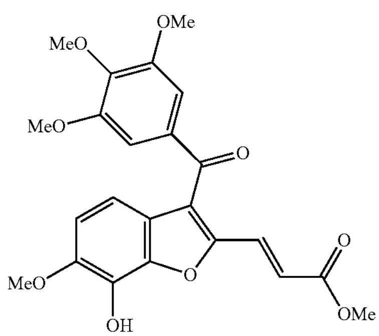 [SMILES: COC(=O)/C=C/c1oc2c(O)c(OC)ccc2c1C(=O)c1cc(OC)c(OC)c(OC)c1] | 2.0 | Tum: 0.1-1  Norm: 1-10 |
| 18 | 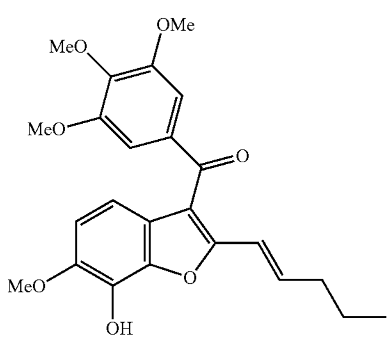 [SMILES: CCC/C=C/c1oc2c(O)c(OC)ccc2c1C(=O)c1cc(OC)c(OC)c(OC)c1] | 8.0 | Tum: 1-10  Norm: 1-10 |

TABLE 1-continued

In Vitro Data for Compounds: These are the results for growth inhibition studies of compounds using the Sulforhodamine B (SRB) or Systmex cell counting (CC) assays. IC$_{50}$ is the concentration required to inhibit net cell growth by 50%.

| Example | Structure | Cancer cell line[a]: IC$_{50}$, nM | HUVECs[c] Tum: IC$_{50}$, nM Norm: IC$_{50}$, nM |
|---|---|---|---|
| 19 | 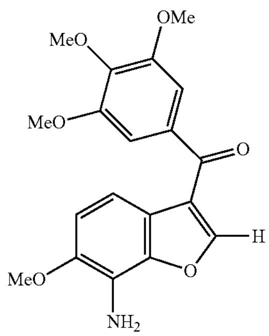 [SMILES: COc1cc(C(=O)c2coc3c(N)c(OC)ccc23)cc(OC)c1OC] | 1-10[b] | Tum: 1-10 Norm: 1-10 |
| 20 | 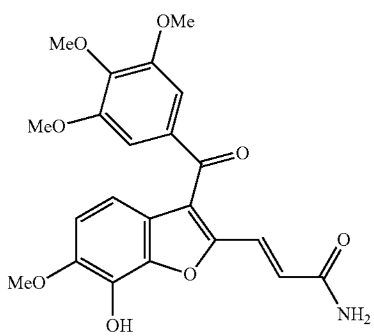 [SMILES: COc1cc(C(=O)c2c(/C=C/C(N)=O)oc3c(O)c(OC)ccc23)cc(OC)c1OC] | 1-10[b] | Tum: 1-10 Norm: 1-10 |
| 21 | 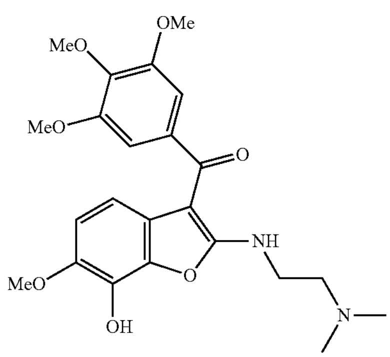 [SMILES: COc1cc(C(=O)c2c(NCCN(C)C)oc3c(O)c(OC)ccc23)cc(OC)c1OC] | 10-100[b] | Tum: 10-100 Norm: 10-100 |
| 22 | 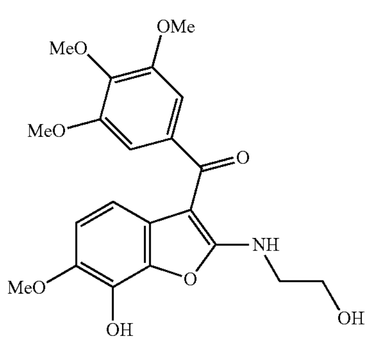 [SMILES: COc1cc(C(=O)c2c(NCCO)oc3c(O)c(OC)ccc23)cc(OC)c1OC] | 1-10[b] | Tum: 1-10 Norm: 1-10 |

TABLE 1-continued

*In Vitro Data for Compounds: These are the results for growth inhibition studies of compounds using the Sulforhodamine B (SRB) or Systmex cell counting (CC) assays. IC$_{50}$ is the concentration required to inhibit net cell growth by 50%.*

| Example | Structure | Cancer cell line[a]: IC$_{50}$, nM | HUVECs[c] Tum: IC$_{50}$, nM Norm: IC$_{50}$, nM |
|---|---|---|---|
| 23 | 3,4,5-trimethoxybenzoyl-(6-methoxy-7-hydroxy-2-cyano-benzofuran-3-yl) ketone | 0.1-1[b] | Tum: 1-10<br>Norm: 1-10 |
| 24 | 3,4,5-trimethoxybenzoyl-(6-methoxy-7-hydroxy-2-methoxycarbonyl-benzofuran-3-yl) ketone | 1-10[b] | Tum: 1-10<br>Norm: 1-10 |
| 25 | 3,4,5-trimethoxybenzoyl-(6-methoxy-7-hydroxy-2-amino-benzofuran-3-yl) ketone | 0.1-1[b] | Tum: 1-10<br>Norm: 1-10 |
| 26 | 3,4,5-trimethoxybenzoyl-(6-methoxy-7-hydroxy-2-(NH-CH$_2$-C(O)-OMe)-benzofuran-3-yl) ketone | 1-10[b] | Tum: 1-10<br>Norm: 1-10 |

TABLE 1-continued

In Vitro Data for Compounds: These are the results for growth inhibition studies of compounds using the Sulforhodamine B (SRB) or Systmex cell counting (CC) assays. IC$_{50}$ is the concentration required to inhibit net cell growth by 50%.

| Example | Structure | Cancer cell line[a]: IC$_{50}$, nM | HUVECs[c] Tum: IC$_{50}$, nM Norm: IC$_{50}$, nM |
|---|---|---|---|
| 27 | (structure: 3-(3,4,5-trimethoxybenzoyl)-2-(pyridin-3-ylamino)-6-methoxy-7-hydroxybenzofuran) | 1-10[b] | Tum: 1-10<br>Norm: 1-10 |
| 28 | (structure: 3-(3,4,5-trimethoxybenzoyl)-2-(dimethylamino)-6-methoxy-7-hydroxybenzofuran) | 1-10[b] | Tum: 1-10<br>Norm: 1-10 |
| 29 | (structure: 3-(3,4,5-trimethoxybenzoyl)-2-(2-(Boc-amino)ethylamino)-6-methoxy-7-hydroxybenzofuran) | | Tum: 1-10<br>Norm: 1-10 |
| 30 | (structure: 3-(3,4,5-trimethoxybenzoyl)-2-(2-aminoethylamino)-6-methoxy-7-hydroxybenzofuran, NH$_2$·HCl) | | Tum: 100-1000<br>Norm: 100-1000 |

TABLE 1-continued

In Vitro Data for Compounds: These are the results for growth inhibition studies of compounds using the Sulforhodamine B (SRB) or Systmex cell counting (CC) assays. IC$_{50}$ is the concentration required to inhibit net cell growth by 50%.

| Example | Structure | Cancer cell line[a]: IC$_{50}$, nM | HUVECs[c] Tum: IC$_{50}$, nM Norm: IC$_{50}$, nM |
|---|---|---|---|
| 31 | 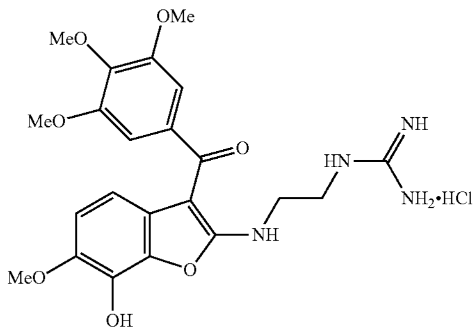 | | Tum: 100-1000<br>Norm: 10-100 |
| 32 | 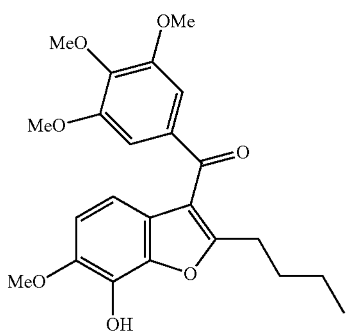 [SMILES: CCCCc1oc2c(O)c(OC)ccc2c1C(=O)c1cc(OC)c(OC)c(OC)c1] | | Tum: 1-10<br>Norm: 1-10 |
| 33 | 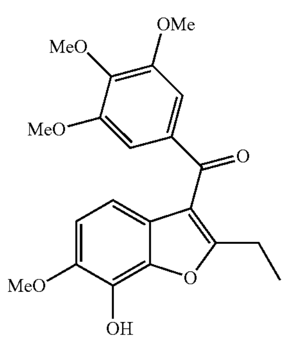 [SMILES: CCc1oc2c(O)c(OC)ccc2c1C(=O)c1cc(OC)c(OC)c(OC)c1] | | Tum: 0.1-1.0<br>Norm: 0.1-1.0 |
| 34 | 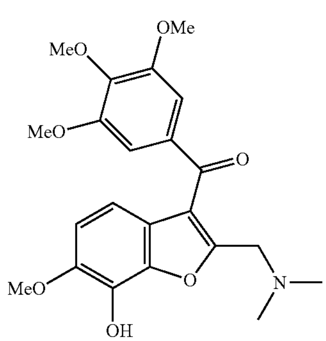 [SMILES: COc1cc(C(=O)c2c(CN(C)C)oc3c(O)c(OC)ccc23)cc(OC)c1OC] | | Tum: 1-10<br>Norm: 1-10 |

TABLE 1-continued

In Vitro Data for Compounds: These are the results for growth inhibition studies of compounds using the Sulforhodamine B (SRB) or Systmex cell counting (CC) assays. $IC_{50}$ is the concentration required to inhibit net cell growth by 50%.

| Example | Structure | Cancer cell line[a]: $IC_{50}$, nM | HUVECs[c] Tum: $IC_{50}$, nM Norm: $IC_{50}$, nM |
|---------|-----------|-----------------------------------|--------------------------------------------------|
| 35 | 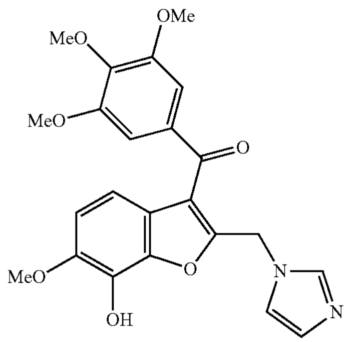 [SMILES: COc1cc(C(=O)c2c(Cn3ccnc3)oc3c(O)c(OC)ccc23)cc(OC)c1OC] | | Tum: 1-10 Norm: 1-10 |
| 36 | 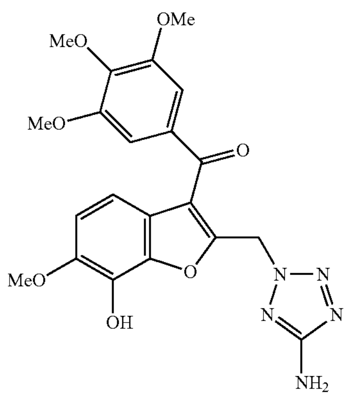 [SMILES: COc1cc(C(=O)c2c(Cn3nnc(N)n3)oc3c(O)c(OC)ccc23)cc(OC)c1OC] | | Tum: 1-10 Norm: 1-10 |
| 37 | 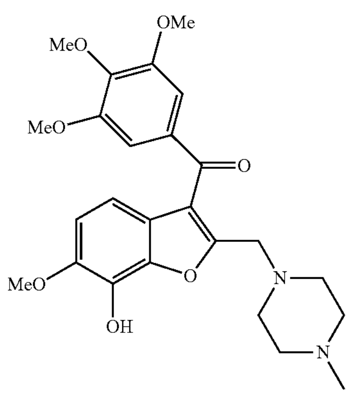 [SMILES: COc1cc(C(=O)c2c(CN3CCN(C)CC3)oc3c(O)c(OC)ccc23)cc(OC)c1OC] | | Tum: 10-100 Norm: 10-100 |
| 38 | 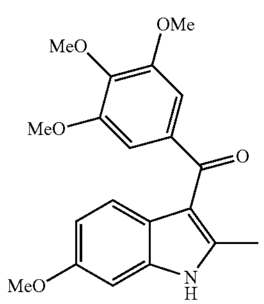 [SMILES: COc1ccc2c(C(=O)c3cc(OC)c(OC)c(OC)c3)c(C)[nH]c2c1] | | Tum: 0.1-1 Norm: 0.1-1 |

TABLE 1-continued

In Vitro Data for Compounds: These are the results for growth inhibition studies of compounds using the Sulforhodamine B (SRB) or Systmex cell counting (CC) assays. IC$_{50}$ is the concentration required to inhibit net cell growth by 50%.

| Example | Structure | Cancer cell line[a]: IC$_{50}$, nM | HUVECs[c] Tum: IC$_{50}$, nM Norm: IC$_{50}$, nM |
|---|---|---|---|
| 39 | 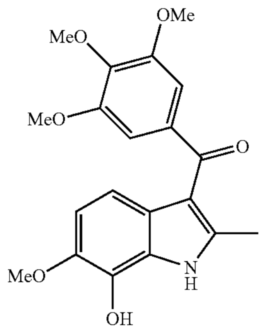 [SMILES: COc1cc(C(=O)c2c(C)[nH]c3c(O)c(OC)ccc23)cc(OC)c1OC] | | Tum: 0.01-0.1 Norm: 0.1-1 |
| 40 | 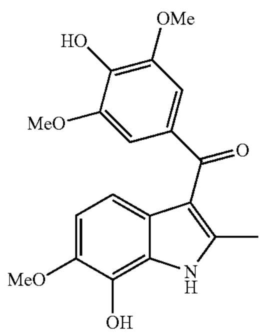 [SMILES: COc1cc(C(=O)c2c(C)[nH]c3c(O)c(OC)ccc23)cc(OC)c1O] | | Tum: 1-10 Norm: 10-100 |
| 41 | 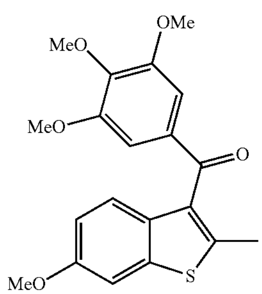 [SMILES: COc1ccc2c(C(=O)c3cc(OC)c(OC)c(OC)c3)c(C)sc2c1] | | Tum: 1-10 Norm: 1-10 |
| 42 | 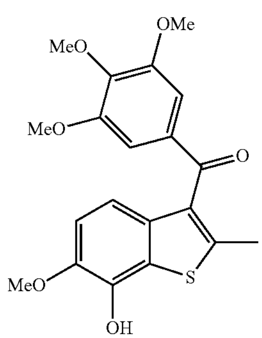 | | Tum: 0.1-1 Norm: 1-10 |

TABLE 1-continued

In Vitro Data for Compounds: These are the results for growth inhibition studies of compounds using the Sulforhodamine B (SRB) or Systmex cell counting (CC) assays. $IC_{50}$ is the concentration required to inhibit net cell growth by 50%.

| Example | Structure | Cancer cell line[a]: $IC_{50}$, nM | HUVECs[c] Tum: $IC_{50}$, nM Norm: $IC_{50}$, nM |
|---|---|---|---|
| 43 | 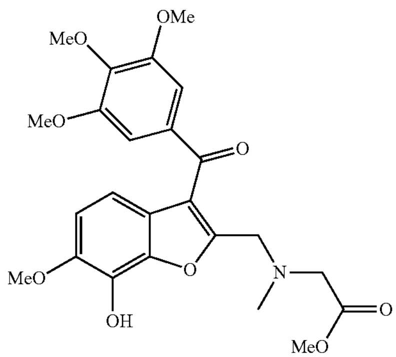 [SMILES: COC(=O)CN(C)Cc1oc2c(O)c(OC)ccc2c1C(=O)c1cc(OC)c(OC)c(OC)c1] | | Tum: 1-10 Norm: 1-10 |
| 44 | 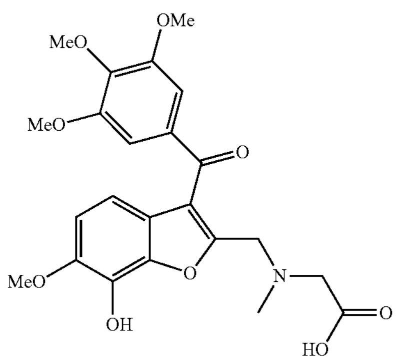 [SMILES: COc1cc(C(=O)c2c(CN(C)CC(=O)O)oc3c(O)c(OC)ccc23)cc(OC)c1OC] | | Tum: 10-100 Norm: 10-100 |
| 45 | 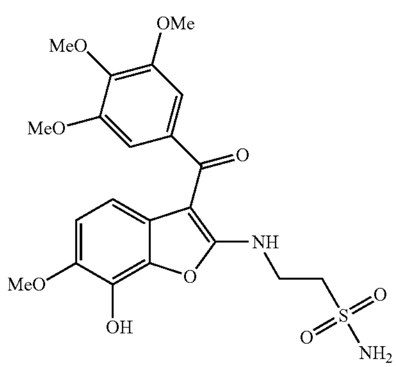 [SMILES: COc1cc(C(=O)c2c(NCCS(N)(=O)=O)oc3c(O)c(OC)ccc23)cc(OC)c1OC] | | Tum: 1-10 Norm: 1-10 |
| 46 | 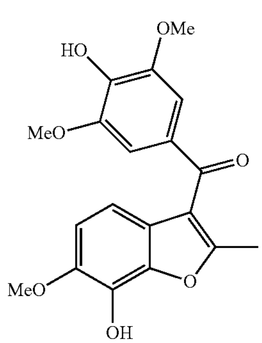 [SMILES: COc1cc(C(=O)c2c(C)oc3c(O)c(OC)ccc23)cc(OC)c1O] | | Tum: 10-100 Norm: 100-1000 |

TABLE 1-continued

In Vitro Data for Compounds: These are the results for growth inhibition studies of compounds using the Sulforhodamine B (SRB) or Systmex cell counting (CC) assays. $IC_{50}$ is the concentration required to inhibit net cell growth by 50%.

| Example | Structure | Cancer cell line[a]: $IC_{50}$, nM | HUVECs[c] Tum: $IC_{50}$, nM Norm: $IC_{50}$, nM |
|---|---|---|---|
| 47 | (structure: 3,4,5-trimethoxybenzoyl linked to 6-methoxyindole at 3-position) | | Tum: 1-10 Norm: 1-10 |

[a]Unless otherwise stated the cancer cell line is MCF-7.
[b]The cancer cell line is MDA-MB-231.
[c]Human umbilical vein endothelial cells (HUVECs) tumour type activated endothelial cells (Tum) and normal quiescent type endothelial cells (Norm).

General Description of Biological Experiments:

Tubulin Polymerisation Assay: Tubulin polymerisation inhibition assays were performed using a fluorescent-based detection kit (#BK011, Cytoskeleton) according to the instructions of the manufacturer. The test compound was added to a 2 mg/ml tubulin solution containing 20% glycerol and 1 mM GTP in 1× Buffer 1 (Buffer 1: 80 mM piperazine-N,N'-bis[2-ethanesulfonic acid]sequisodium salt; 2 mM magnesium chloride; 0.5 mM Ethylene glycol-bis(b-aminoethyl ether)N,N,N',N'-tetra-acetic acid, pH 6.9, 10 uM fluorescent reporter). Fluorescence was measured over a period of 42 minutes at 1 minute intervals. Increased fluorescence indicates increase in tubulin polymerisation. There is a tenfold increase in the affinity of the fluorescent reporter for polymerised tubulin compared to monomeric tubulin subunits. The result is a fluorescence signal that closely follows tubulin polymerisation.

Proliferation Assay—quiescent endothelium: Human umbilical vein endothelial cells (CC-2519, Clonetics) were plated at 15000 cells/well in EBM2 (CC-3156, Clonetics)+ 0.5% FBS (CC-4101A, Clonetics)+GA-1000 (CC-4381A, Clonetics) in a 96 well plate in triplicate. Cells were cultured overnight at 37° C. 5% $CO_2$. Medium was subsequently replaced with fresh medium including the compound or negative control. Cells were cultured for a period of 48 hrs. An MTT assay was performed to measure changes in cell numbers. Briefly, 20 µl of MTT reagent was added to cells containing 100 µl of EBM2+0.5% FBS and incubated at 37° C. for 2 hours. Absorbance was measured at 492 nm.

Proliferation Assay—activated endothelium: Human umbilical vein endothelial cells (CC-2519, Clonetics) were plated at 2500 cells/well in EGM2 (CC-3162, Clonetics) in a 96 well plate in triplicate. Cells were cultured overnight at 37° C. 5% $CO_2$. Medium was subsequently replaced with fresh medium including the compound or negative control. Cells were cultured for a period of 48 hrs. An MTT assay was performed to measure changes in cell numbers. Briefly, 20 µl of MTT reagent was added to cells containing 100 µl of EGM2 and incubated at 37° C. for 2 hours. Absorbance was measured at 492 nm.

(ii) In Vivo Studies for Combination Partner (a)

Figure 4:
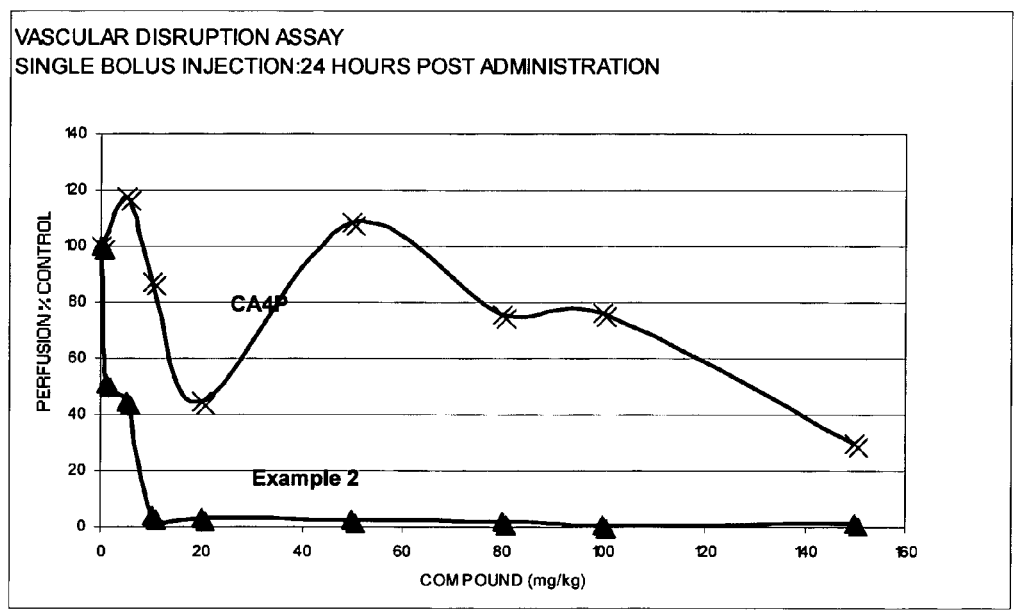
FIG. 4 Depicts a graph of % perfusion control against an amount of compound (mg/kg) in relation to comparative levels of vascular shutdown (reduction in tumour perfusion) between CA4P and compound Example 2 of the present invention.

Vascular Disruption Assay: Female athymic BALB/c-nu/nu mice (nude mice) were used for this study. Mice were between 6-8 weeks old and were purchased from the Animal Resource Centre, Perth, Western Australia and allowed to acclimatize for a couple of days. All the animals were housed under pathogen-free conditions and cared for in accordance with Flinders University of South Australia and NH&MRC guidelines and the Australian Code of Practice for the care and use of animals for scientific purposes. The human breast cancer MDA MB 231 was grown as orthotopic xenografts in the mammary fat pad of nude mice. Each mouse was injected with $2 \times 10^6$ cells in 50 µl Dulbecco's PBS subcutaneously just above the mammary fat pad, below the right forward limb. Tumors were selected for treatment when they reached a diameter of 100-150 mm³ (3 weeks after implantation). The test compound (Example 2) was dissolved in saline solution and injected intravenously at concentrations ranging from 150 mg/kg-1 mg/kg in a total volume of 400 ul. Tumor bearing animals were injected intravenously with 10 mg/kg Hoechst 33342, 24 hours after the injection of the test compound. Animals were euthanised 1 minute after the Hoechst 33342 injection. Tumors were recovered for histochemical analysis. Tumor perfusion analysis was performed by assessing the amount of Hoechst 33342 staining across an entire tumor cross-section. 10 micron sections of frozen tumor biopsies were viewed under an ultraviolet light filter. Using a 4× objective lens, 8-bit monochromatic images were captured in succession, representing the total area of the tumor section. Composite images of the total tumor section were generated by overlaying common areas of the monochromatic images. Hematoxylin and Eosin-Y staining of the same tumor section was performed to identify non-tumor regions. Non-tumor regions were mapped on Hoechst 33342 composite images and excluded from the quantitation analysis. Quantitation was performed by measuring the pixel area of Hoechst 33342 staining and the total pixel area of the tumor region. Perfusion was expressed as a percentage of Hoechst 33342 stained area to total tumor area (see FIG. 4).

Tumor Growth Inhibition: Balb/c nu/nu mice bearing MDA-MB-231 solid orthotopic tumors were treated with compound Example 2 at 40 mg/kg. Animals were i.v. dosed with a total of two cycles of Example 2 treatment. Each cycle was dosing on days and 8 followed by a three week no-dosing period. Tumor growth represented as a ratio to initial tumor volume is shown over a total of 72-days.

Figure 5:
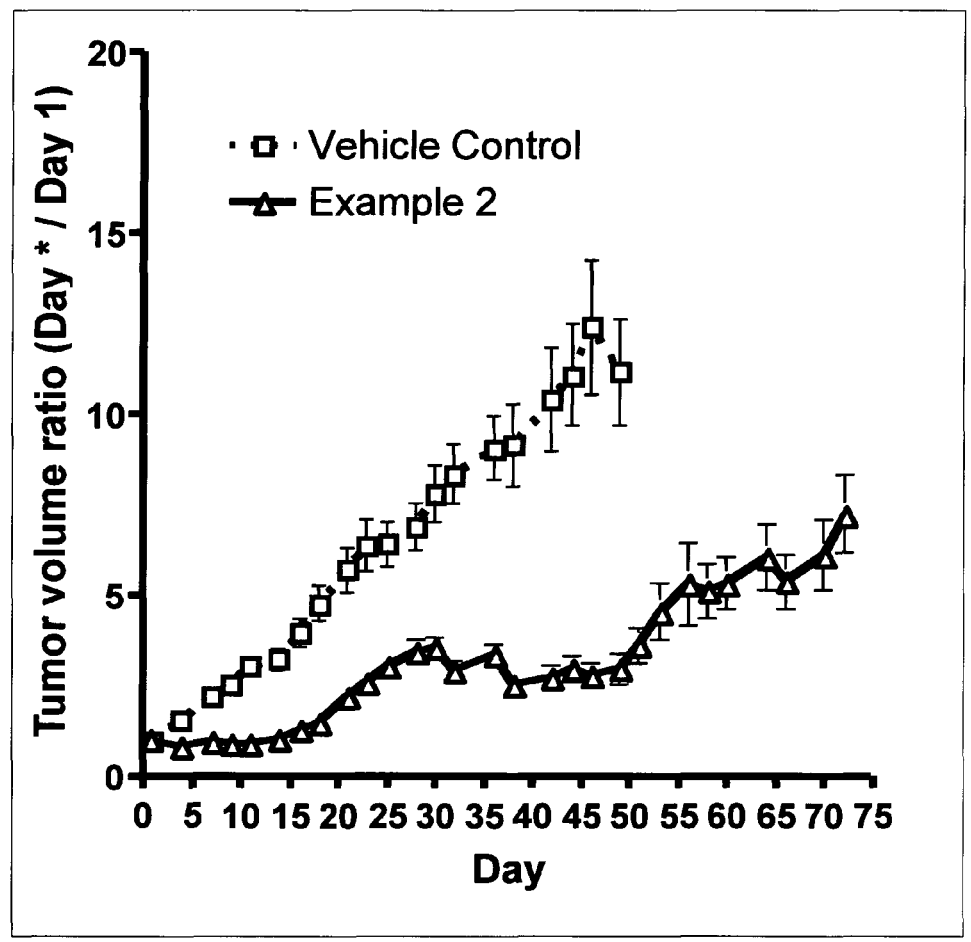
FIG. 5 Depicts a graph of Tumor Volume ratio (Day*/Day 1) against time (Days) in relation to tumor growth inhibition of compound Example 2 in Balb/c nu/nu mice bearing MDA-MB-231 orthotopic breast solid tumors.

Tumor growth as well as animal health were monitored for up to 72 days post-day 1 of treatment. The results seen in this experiment (see FIG. 5) clearly show tumor growth inhibition in animals treated with two cycles of Example 2. Significant differences in tumor growth between Example 2 treated (n=64) and vehicle treated (n=20) animals were observed as early as day 4 (p<0.001; unpaired t-test; Prism® analysis) through to Day 70.

(B) (i) In Vitro Studies for Combinations of (a) and (b)

Preclinical evaluation of tubulin targeting VDA agents has demonstrated that these compounds are able to disrupt tumor blood flow, increase tumor hypoxia and necrosis. These effects result in some reduction of tumor growth in animal models. Tumor recovery from the vascular damage caused by VDA action occurs within 48 hrs post-treatment. Furthermore, vascular disruption spares the outer cellular rim of a tumor mass that appears to be supported by normal vessels that surround the tumor capsule and remain unaffected by VDA action. It is reasonable to hypothesise that his viable rim subsequently supports tumor revascularisation and recovery from the action of the VDA agent. We hypothesised that the recovery of the tumors from the effects of the VDA action is driven by molecular pathways that support cancer cell survival and induction of angiogenesis. We undertook a number of histological analyses to assess the damage caused by Example 2 on the integrity of components of the tumor microenvironment and obtain information of upregulation of proteins that are likely to be involved in tumor recovery. Our analyses included evaluation of the expression of VEGF, phosphorylated mTOR, Hypoxia inducible factor-1-alpha (Hif-1$\alpha$), and Hypoxia inducible factor-2-alpha (Hif-2$\alpha$), the level of apoptosis, integrity of endothelial cells and the basement membrane protein laminin. Our observations demonstrate that 24-30 hrs following treatment with Example 2 there is a decrease in staining with the endothelial cell marker, and CD31, attesting to the destruction of tumor endothelial cells, and considerable reduction in the staining of laminin, which is evidence of degradation of the basement membrane integrity. Furthermore, our analyses showed a significant increase in the number of apoptotic cells within the tumor. Most importantly a dramatic increase in staining with the anti-human VEGF antibody was evident. Increased expression of phosphorylated mTOR (ser 2448), Hif-1$\alpha$ and Hif-2$\alpha$ around the viable rim region as indicated by arrows and loss of endothelial cells in the necrotic zone (as indicated by arrow in FIG. 3) is seen in Example 2 treated tumors.

The novel finding of phosphorylated mTOR upregulation in the viable rim surrounding Example 2 induced necrotic tumor regions gives rise to the current hypothesis that combination of Example 2 (and like, TPI agents) treatment with inhibitors of the mTOR protein will synergise in delivering a prolonged vascular shutdown effect exposing the tumor to longer periods of hypoxia and resulting in increased suppression of tumor growth.

Furthermore, the inherent property of tubulin targeting agents to suppress cancer cell proliferation provides a secondary anticancer mechanism for this class of agents. We have demonstrated that combination treatment of a number of cell lines with Example 2 and the inhibitor of mTOR temsirolimus produces additive effects in suppressing cancer cell line proliferation in vitro. In addition to its demonstrated role in inducing angiogenesis, mTOR is also a key driver of cancer cell metabolism and survival. Inhibitors of mTOR induce cytostasis and a number have been approved for clinical use in a number of cancer settings. Thus, concurrent targeting of tubulin and mTOR is likely to yield improved therapeutic benefit.

The dual mode of potential therapeutic compatibility of mTOR with TPI agents through disruption of tumor vascular support and directly through suppression of cancer cell proliferation is unique to the TPI class of tubulin targeting compounds. In contrast, non-TPI agents with VDA activity for example, DMXAA or ASA404 (5,6-dimethylxanthenone-4-acetic acid) do not exert direct anti-proliferative action on cancer cells.

Figure 3:
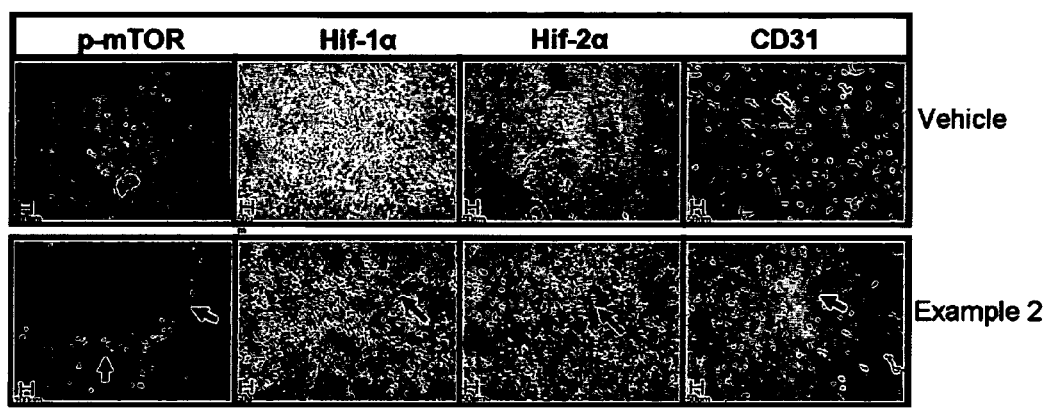
FIG. 3 Image depicting immunochemistry analysis of human renal xenografts treated with Example 2.

Immunohistochemistry Analysis—Method (FIG. 3)

Female BALB/c nu/nu mice at 6 to 8 weeks were injected s.c. with the human cancer cell line Caki-1 representing renal cancer. Cells were resuspended in Dulbecco's PBS (Sigma-Aldrich) and $5\times10^6$ cells were injected s.c. Tumors were grown to an average size of 700 mm$^3$ prior to treatment. Example 2 treatment consisted of a single i.v. injection at dose level of 32 mg/kg. Saline treatment was included as a vehicle control. Animals were euthanized and tumors were excised for histologic examination 24 hours post dosing. Cryosections of tumors were prepared and probed with phosphorylated mTOR (ser 2448), Hif-1$\alpha$, Hif-2$\alpha$ and CD31 specific antibodies. Antibody staining was visualized using 3,3'-Diaminobenzidine (brown staining) and sections were conterstained with Myers hematoxylin.

Assessment of Combining Example 2 with mTOR Inhibitors Using an in vitro Proliferation Assay Human cancer cell lines were used to evaluate suitable agents for combination with Example 2.

Analysis was based on measurements of in vitro cell proliferation in the presence of the compounds under evaluation. Cells were seeded at an average of 500-2000 cells/well in 96 well plates allowed to adhere overnight before addition of the test compounds. Cell proliferation was assessed after 48-72 hrs of culture in the presence of the test substances. Cells were treated with a combination of Example 2 and the compound under evaluation, or with each of these agents alone. Proliferation measurements were carried out by a tetrazolium-based colorimetric assay (MTS). Metabolically active cells were measured using CellTiter 96® Aqueous One Solution (Promega Corp. Madison Wis., USA) according to the manufacturers instructions and absorbance readings taken at 492 nm. Absorbance readings for each compound concentration were normalized to corresponding vehicle control cultures. A sigmoidal dose response curve was fitted to the data, and the concentration at which proliferation decreased by 50% was calculated using Graph Pad Prism 4 software (San Diego, USA).

Combination Index Values

Human cancer cell lines (list cell lines: Caki-1, A498, Calu-6, SKOV-3, A4549) were used to evaluate combination treatments in vitro. Cells were treated concurrently with Example 2 with temsirolimus for 72 hours and the ED50 and ED75 data from both the single agents and the combination were analyzed using the quantitative software CalcuSyn to determine the combination index (CI) and effects classified as synergistic, additive or of no additive benefit combinations (Chou T C. *Theoretical basis, experimental design, and computerized simulation of synergism and antagonism in drug combination studies. Pharmacol Rev.* 2006 September; 58(3):621-81). The results are tabulated in FIG. 2.

Cell Culture and Cell Lines

Cancer cell lines included Calu-6, A549, A498, Caki-1, and Sk-OV-3 (ATCC, Manassas, Va., USA). Calu-6, cells were cultured in MEM media (Gibco®) with 10% FCS, 2 mM penicillin-streptomycin-glutamine (Gibco®), 10 mM Hepes buffered solution (Gibco®), 1 mM sodium pyruvate solution (Gibco®) and 0.1 mM non-essential amino acids solution (Gibco®). SK-OV-3 cells were cultured in DMEM/F12 (Gibco®) media with 10% FCS, 2 mM penicillin-streptomycin-glutamine and 10 mM Hepes buffered solution. A549 cells were cultured in F12K (Gibco®) media with 10% FCS and 2 mM penicillin-streptomycin-glutamine. A498 cells were cultured in MEM media (Gibco®) with 10% FCS and 2 mM penicillin-streptomycin-glutamine. Caki-1 cells were cultured in McCoys 5a (Gibco®) media with 0% FCS and 2 mM penicillin-streptomycin-glutamine.

Assessment of Combining Example 2 with mTOR Inhibitors Using an in vivo (Mice) Assay Female BALB/c nu/nu mice at 6 to 8 weeks were s.c. inoculated with the human cell line caki-1 derived from a renal cancer to establish solid tumors. Tumors were grown to an average size of 150 mm³ before commencing treatment. Tumor volume (in cubic millimeters) was measured two to three times per week. Animals were iv dosed Example 2 at 32 mg/kg on Day 1 and Day 8 of 28 day cycle and/or ip dosed Rapamycin at 1 mg/kg on Day 2 and Day 5 of a weekly cycle. Tumour growth and animal health was monitored over the course of the study.

Tumor growth is represented as mean tumor volume in mm³ and graphed up to time point where up to 90% of vehicle treated animals are still living. Survival is shown as a percent of animal still alive and data is shown up until study termination.

Figure 6:
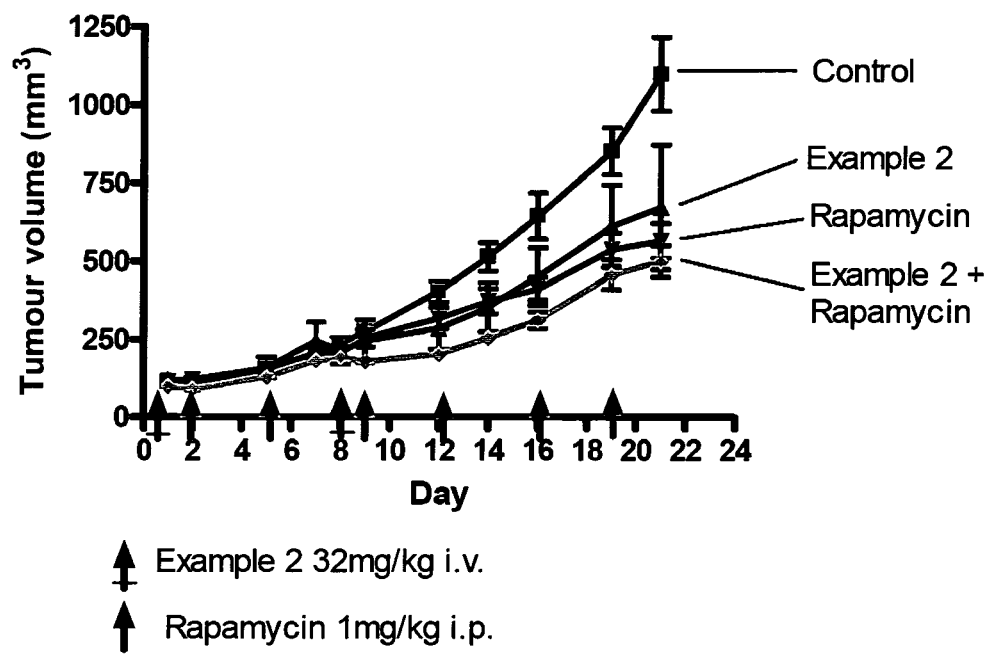
FIG. 6 Depicts a graph of Tumor Volume ($mm^3$) against time (Days) of Caki-1 xenografts treated with Example 2 and mTOR inhibitor rapamycin (+/−SEM).
Figure 7:
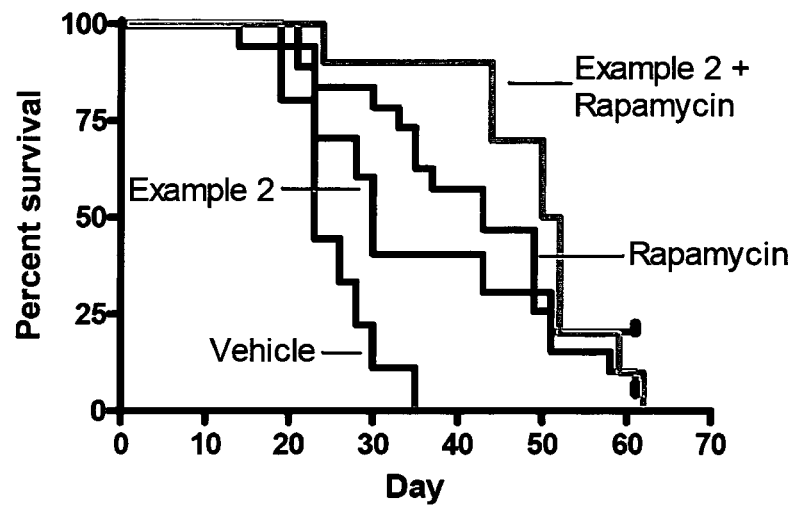
FIG. 7 Depicts a graph of percent survival against time (Days) for the survival of mice having Caki-1 xenografts treated with Example 2 and mTOR inhibitor rapamycin.

A trend towards reduced tumor volume (FIG. 6) and increased survival (FIG. 7) is seen in the combination therapy group (Example 2+Rapamycin) compared to monotherapies alone (Example 2 or Rapamycin) or vehicle control with this scheduling of agents.

The invention claimed is:

1. A method for treating a proliferative disease, comprising administering to a patient in need thereof an effective amount of (a) a tubulin polymerisation inhibitor (TPI), and (b) mTOR inhibitor, wherein the TPI is a compound of formula (III):

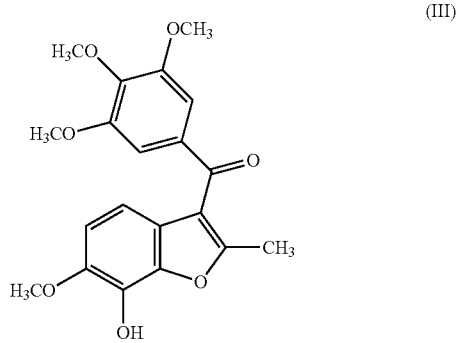 [SMILES: COc1cc(C(=O)c2c(C)oc3c(O)c(OC)ccc23)cc(OC)c1OC]

(III)

or a salt, solvate or disodium phosphate ester prodrug thereof, and the mTOR inhibitor is everolimus, wherein the TPI is administered intravenously at a dose level of between 4 to 16 mg/m².

2. The method according to claim 1, wherein the TPI is administered intravenously at a dose level of between 4 to 16 mg/m², and the mTOR inhibitor is administered as an oral dose.

3. The method according to claim 2, wherein the mTOR inhibitor is administered as an oral daily dose.

4. The method according to claim 1, wherein the TPI is administered intravenously at a dose level of between 4 to 16 mg/m² on days 1 and 8 of a 21-day cycle, and the mTOR inhibitor is administered as an oral daily dose.

5. The method according to claim 1, wherein the proliferative disease is cancer.

6. The method according to claim 1, wherein the compound of formula (III) is a compound of formula:

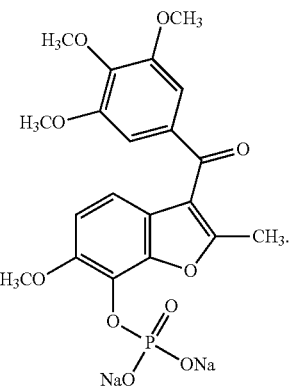

7. The method according to claim 1, wherein the proliferative disease is selected from the group consisting of renal cancer, ovarian cancer, breast cancer, and lung cancer.

8. The method according to claim 7, wherein the proliferative disease is renal cancer.

9. The method according to claim 7, wherein the proliferative disease is breast cancer.

10. The method according to claim 1, wherein (a) TPI and (b) mTOR inhibitor are administered separately.

11. The method according to claim 10, wherein (b) mTOR inhibitor is administered prior to (a) the TPI.

* * * * *